United States Patent [19]
Ophir et al.

[11] Patent Number: 5,474,070
[45] Date of Patent: Dec. 12, 1995

[54] METHOD AND APPARATUS FOR ELASTOGRAPHIC MEASUREMENT AND IMAGING

[75] Inventors: Jonathan Ophir; Ignacio Cespedes, both of Houston, Tex.

[73] Assignee: The Board of Regents of the University of Texas System, Tex.

[21] Appl. No.: 212,734

[22] Filed: Mar. 11, 1994

Related U.S. Application Data

[63] Continuation-in-part of Ser. No. 940,182, Sep. 3, 1992, Pat. No. 5,293,870, which is a continuation-in-part of Ser. No. 535,312, Jun. 8, 1990, Pat. No. 5,107,837, which is a continuation-in-part of Ser. No. 438,695, Nov. 17, 1989, Pat. No. 5,143,070.

[51] Int. Cl.⁶ .................................................. A61B 8/00
[52] U.S. Cl. ............................. 128/660.01; 128/661.03
[58] Field of Search ..................... 128/660.01, 660.06, 128/660.07, 661.03, 660.08; 73/597

[56] References Cited

U.S. PATENT DOCUMENTS

| | | | |
|---|---|---|---|
| 5,143,070 | 9/1992 | Ophir et al. | 128/660.01 |
| 5,178,147 | 1/1993 | Ophir et al. | 128/660.01 |
| 5,293,870 | 3/1994 | Ophir et al. | 128/660.01 |

OTHER PUBLICATIONS

C. E. Jamison, et al., 1968, "Viscoelastic Properties of Soft Tissue by Discrete Model Characterization", J. Biomechanics, vol. 1, pp. 33–46.

Hilmi Demiray, 1972, "A Note on the Elasticity of Soft Biological Tissues", J. Biomechanics, vol. 5, pp. 309–311.

Roderic S. Lakes, et al., 1974, "Interrelationships Among the Viscoelastic Functions for Anisotropic Solids: Application to Calcified Tissues and Related Systems", J. Biomechanics, vol. 7, pp. 259–270.

J. R. Parsons et al., 1977, "The Viscoelastic Shear Behavior of Normal Rabbit Articular Cartilage", Biomechanics, vol. 10, pp. 21–29.

Stanton A. Glantz, 1977, "A Threep–Element Description for Muscle with Viscoelastic Passive Elements", Biomechanics, vol. 10, pp. 5–20.

W. F. Decraemer, et al., 1980, "A Non–Linear Viscoelastic Constitutive Equation for Soft Biological Tissues, Based Upon a Structural Model", Biomechanics, vol. 13, pp. 559–564.

P. H. DeHoff, 1978, "On the Nonlinear Viscoelastic Behavior of Soft Biological Tissues", Biomechanics, vol. 11, pp. 35–40.

Allen H. Hoffman, et al., 1984, "A Method for Measuring Strains in Soft Tissue", Biomechanics, vol. 17, No. 10, pp. 795–800.

T. R. Fenton, et al.,1984, "Collapse and Viscoelasticity of Diseased Human Arteries", J. Biomechanics, vol. 17, No. 10, pp. 789–793.

C. J. Chuong, et al., 1984, "Compressibility and Constitutive (List continued on next page.)

Primary Examiner—Francis Jaworski
Attorney, Agent, or Firm—Rosenblatt & Associates

[57] ABSTRACT

An improved ultrasonic pulse-echo method and apparatus that has particular application in making precision measurements of compressibility in any backscattering material, in particular organic tissue, is disclosed. The method employs a standard transducer or transducer containing device which is translated transaxially, thereby compressing or displacing a proximal region of a target body in small known increments. At each increment, a pulse is emitted and an echo sequence (A-line) is detected from regions within the target along the sonic travel path or beam of the transducer. Resulting time shifts in echo segments corresponding to features in the target, corrected for regions of varying sonic speed along the sonic path, provide relative and quantitative information concerning the strain caused by the compressions. The stress imparted by the transducer and containing device is also determined, corrected for depth along the sonic path. The appropriate values for stress are divided into the respective values for strain along each path to yield an elastogram, or array of compressibility values, of the target.

20 Claims, 11 Drawing Sheets

OTHER PUBLICATIONS

Equation of Arterial Wall in Radial Compression Experiments", J. Biomechanics, vol. 17, No. 1, pp. 35–40.

Howard M. Loree, et al., Oct. 1992, "Effects of Fibrous Cap Thickness on Peak Circumferential Stress in Model Atherosclerotic Vessels", Circulation Research, vol. 71, No. 4, pp. 850–858.

Richard T. Lee, et al., May 1991, "Structure–Dependent Dynamic Mechanical Behavior of Fibrous Caps from Human Atherosclerotic Plaques", Circulation, vol. 83, No. 5, pp. 1764–1770.

P. D. Richardson, et al., Oct. 21, 1989, "Influence of Plaque Configuration and Stress Distribution on Fissuring of Coronary Atherosclerotic Plaques", The Lancet, pp. 941–944.

Richard T. Lee, et al., Jan. 1992, "Prediction of Mechanical Properties of Human Atherosclerotic Tissue by High–Frequency Intravascular Ultrasound Imaging", Arteriocloerosis and Thrombosis, vol. 12, No. 1, pp. 1–5.

Mannan Mridha, et al., 1992, "Mechanical Pulse Wave Propagation in Gel, Normal and Oedematous Tissues", J. Biomechanics, vol. 25, No. 10, pp. 1213–1218.

A. K. Tsaturyan, et al., 1984, "Extracellular Fluid Filtration as the Reason for the Viscoelastic Behaviour of the Passive Myocardium", J. Biomechanics, vol. 17, No. 10, pp. 749–755.

Arthur C. Guyton, et al., Aug. 1966, "Interstitial Fluid Pressure: III, Its Effect on Resistance to Tissue Fluid Mobility", Circulation Research, vol. XIX, pp. 412–419.

Robert A. Brace, et al., 1979, "Interstitial Fluid Pressure: Capsule Free Fluid, gel Fluid and Gel Absorption Pressure in Subcutaneous Tissue", Microvascular Reserch, vol. 18, pp. 217–228.

Barry B. Goldberg, et al., Apr. 1990, "Endoluminal US: Experiments with Nonvascular Uses in Animals", Radiology, vol. 174, No. 3, pp. 39–43.

Cynthia J. McCormack, et al., 1990, "Chemical and Physicochemical Comparison of Advanced Atherosclerotic Lesions of Similar Size and Cholesterol Content in Cholesterol–fed New Zealand White and Watanabe Heritable Hyperlipidemic Rabbits", Laboratory Investigation, vol. 62, No. 2, pp. 213–222.

David A. Waugh, et al., 1989, "Physico–chemical Properties of Cholesterol–Fed Rabbit β–VLDL are not Affected by Different Dietary Oils", Atherosclerosis, vol. 76, pp. 237–243.

METHOD AND APPARATUS FOR ELASTOGRAPHIC MEASUREMENT AND IMAGING

This application is a continuation-in-pan of application Ser. No. 940,182, filed Sep. 3, 1992, and now U.S. Pat. No. 5,293,870 which is a continuation-in-pan of application Ser. No. 535,312, filed Jun. 8, 1990, which issued as U.S. Pat. No. 5,107,837, and which is a continuation-in-part of application Ser. No. 438,695, filed Nov. 17, 1989, which issued as U.S. Pat. No. 5,143,070. Applicant incorporates application Ser. Nos. 940,182, 535,312, and 438,695, by reference, and claims the benefit of said applications for all purposes pursuant to 37 CFR §1.78.

The U.S. Government may own rights in this application and patents that may issue therefrom pursuant to N.I.H. grants R01-CA38515 and R01-CA44389.

BACKGROUND OF THE INVENTION

1. Field of the Invention

This invention relates generally to a method and apparatus for performing elastographic diagnosis of a target body. Elastography is a system for measuring and imaging elastic modulus and compressibility distributions in an elastic tissue. It also has application to strain profiling and improved sonographic measurement and imaging. This system is typically based on external compression of a target body, and utilizes one or more transducers, acting as or with a compressor, to generate pre- and post-compression sonic pulses and receive the resulting echo sequences (A-lines) from within the target body. The pre- and post-compression echo sequence pairs may then be cross-correlated or matched to determine the strain along the path of the sonic pulses, and preferably to yield a strain profile of the target body. This strain profile may then be converted into a compressibility profile or elastogram by measuring the stress imposed by the compressing device and calculating the elastic moduli based on the stress and the strain profile.

An elastogram may be considered to be a special form of multi-trace sonogram, wherein each trace is a record or display with depth within a target body of an elastic modulus function of the body. A preferred elastic modulus function for purposes of display is the inverse of the bulk modulus, which provides a measure of compressibility. As explained later in this description, the inverse of the Young's moduli may usually be used instead of the bulk moduli. Less preferred but also helpful are the Young's moduli themselves. Methods for making and using elastograms are described at length in copending application Ser. No. 7/535,312.

While the methods described in application Ser No. 7/535,312 produce greatly improved records and understanding of structures of elastic tissues, it has been observed that certain inaccuracies in the resulting elastograms may arise. In particular, inaccuracies have been observed if the transducer and compressor used to compress and insonify a tissue are relatively small in size relative to the depth (or thickness) of the target body, giving rise to decreasing stress in the target body as the distance increases from the compressor. Likewise, inaccuracies have been observed in elastograms and sonograms if the target body is not relatively homogeneous with respect to sonic speed, giving rise to strata through which sonic pulses travel at differing velocities. The improved methods and apparatus for elastography disclosed herein, while generally enhancing the accuracy of elastograms, have particular application in reducing the effect of such inaccuracies in both elastograms and sonograms.

2. Related Art

Traditional ultrasonic diagnosis is achieved by transmitting ultrasonic energy into a target body and generating an image from the resulting echo signals. A transducer is used to both transmit the ultrasonic energy and to receive the echo signals. During transmission, the transducer converts electrical energy into mechanical vibrations. Acquired echo signals produce mechanical oscillations in the transducer which are reconverted into electrical signals for amplification and recognition.

A plot or display (e.g., on an oscilloscope, etc.) of the electrical signal amplitude versus echo arrival time yields an amplitude line (A-line) or echo sequence corresponding to a particular ultrasonic transmission. When the A-line is displayed directly as a modulated sinusoidal pattern at radio frequency ("RF"), it is typically referred to as an RF or "undetected" signal. For imaging, the A-line is often demodulated to a non-RF or "detected" signal.

Ultrasound techniques have been extensively used in the field of diagnostic medicine as a non-invasive means of analyzing the properties of tissue in vivo (i.e., living). A human or animal body represents a nonhomogeneous medium for the propagation of ultrasound energy. Acoustic impedance changes at boundaries of regions having varying densities and/or sound speeds within such a target body. At such boundaries, a portion of the incident ultrasonic beam is reflected. Inhomogeneities within the tissue form lower level scatter sites that result in additional echo signals. Images may be generated from this information by modulating the intensities of pixels on a video display in proportion to the intensity of echo sequence segments from corresponding points within the target body.

Conventional imaging techniques are widely used to evaluate various diseases within organic tissue. Imaging provides information concerning the size, shape, and position of soft tissue structures using the assumption that sound velocity within the target is constant. Qualitative tissue characterization is carried out by interpretation of the grey scale appearance of the sonograms. Qualitative diagnosis largely depends on the skill and experience of the examiner as well as characteristics of the tissue. Images based only on relative tissue reflectivity, however, have limited use for quantitative assessment of disease states.

Techniques for quantitative tissue characterization using ultrasound are needed for more accurate diagnosis of disorders. In recent years many significant developments have been achieved in the field of ultrasonic tissue characterization. Some acoustic parameters, e.g., speed of sound and attenuation, have been successfully used for tissue characterization.

Tissue compressibility is an important parameter which is used to detect the presence of diffuse or localized disease. Measuring changes in compressibility becomes important in the analysis of tissue for pathological conditions. Many tumors are firmer than the surrounding normal tissue, and many diffuse diseases result in firmer or more tender pathology. Examples can be found in diffuse liver disease, prostate cancer, uterine fibroids, muscle conditioning or disease, breast cancer disease, and many other conditions.

Traditionally, physicians routinely palpate various regions of a patient's body to get an impression of tissue firmness or tissue softness. This technique is a form of remotely trying to sense what is going on in terms of tissue compliance. For example, in a liver, if the compliance in an area is sensed to be different from compliance in the surrounding area, the physician concludes from the tactile sensations in his fingers that something is wrong with the patient. The physician's fingers are used to perform a qualitative measurement.

In the last several years, a number of articles have appeared in the literature that explore various techniques for measurement and imaging of soft tissue compliance and tissue motion using ultrasound. These techniques rely on one of the following procedures: Doppler ultrasound velocity measurements, cross-correlation techniques to quantify motion in tissues, and visual inspection of M-mode and B-mode images. Additionally a Fourier feature extraction technique has been proposed. Internal mechanical excitation (motion of cardiac structures, arterial pulsation) or external vibration sources of motion produce displacement of the tissues under investigation. The displacements of different tissues are then analyzed by one of these techniques.

The amplitude and velocity of motion induced by arterial pulsation is generally too low for evaluation with Doppler velocity measurements. However, a number of researchers have used pulsed Doppler and color flow Doppler systems in conjunction with external mechanical harmonic excitations to determine the elastic properties of tissue. Using a low frequency external excitation source, the velocity of propagation of mechanical waves has been measured and relates to the modulus of elasticity of the tissues. The velocity of vibration of tissues under low frequency vibration excitation has been used to determine their relative compressibility. This technique has been termed "sonoelasticity" and produces B-scans which are "stained" with color coded relative compressibility information. Sophisticated Young's modulus measurements have been applied to determine muscle elasticity as a function of contractility state by measuring Doppler shifts due to very low frequency excitations (10 Hz). A similar approach using vibrations in the 100–1000 Hz range has been proposed to study dynamic muscle elasticity in vivo.

Cross-correlation techniques allow the use of either internally or externally generated sources of mechanical excitation due to their ability to quantify minute motions of tissue. External harmonic excitation has been used to assess motion of soft tissues with one dimensional and two dimensional correlators. The displacement and/or velocity of internally generated motion also have been measured using one dimensional and two dimensional correlators. Tissue strain caused by arterial pulsation in the liver and by transmitted cardiac motion in fetal lung have been proposed for tissue characterization.

Visual inspection of ultrasound M-mode waveforms has been used to study benign and malignant lesions in liver, pancreas and breast and to observe the elasticity of fetal lung. In magnified B-scans of the fetal thorax paracardiac lung movements have been measured to classify fetal lungs as stiff, intermediate or compliant. The examination of fetal lung sonograms has been used to evaluate compressibility as an indicator of lung tissue maturity.

But, one of the main difficulties in these methods is the lack of definition of the magnitude and direction of the driving force. This difficulty applies to driving forces that are internally generated by the pulsations of the heart and/or the aorta, as well as to those applied externally at low frequency and limited directivity. Further, it is difficult to measure the shape of an internal driving force, limiting the ability to determine how stress resulting from the driving force decreases as a function of distance from the driving force. The inability to define the direction, magnitude and shape of the driving force limits the ability of these methods to provide quantitative information about the elastic properties of the tissue under investigation.

SUMMARY OF THE INVENTION

In contrast to these methods, elastography is not limited by a lack of definition of the magnitude, direction or shape of a driving force. Elastography preferably uses an external stimulus of known quantity, such as compression of the target body by a known amount or known stress by a compressor, preferably along with cross correlation or least-means-square matching techniques to generate strain profiles of the tissue under investigation. From these strain profiles and the measurement of the stress applied by the compressor, an elastogram (or image of the inverse elastic modulus profile) is determined. The inverse of the elastic modulus profile is typically displayed on the elastogram because strain measurements may be zero, yielding an elastogram with an infinite range of elastic moduli.

Thus, elastography provides a pulse-echo system that has particular application in estimating and imaging compressibility in a target body. The target body may be any animal or human tissue, or any organic or inorganic substance that is compressible or compliant. The term "animal tissue" includes "human tissue". An ultrasonic source is used to interrogate the target body. The detection of echo sequences may be at the ultrasonic source. Thus, elastography allows for accurate, localized determination and imaging of an important parameter, compressibility, which has been used qualitatively in medicine for a very long time.

Compressibility of a material is normally defined as the inverse of the bulk modulus of the material. The bulk modulus of a volume may be determined by the following formula:

$$BM = P/(\Delta V/V) \qquad \text{Equation 1}$$

where

BM = Bulk modulus

P = the pressure or stress on a tissue segment of interest $(\Delta V/V)$ = the volumetric strain of a tissue segment of interest, where $\Delta V$ = a change in the volume of the segment, and V = the original volume of the segment.

In a preferred method of elastography where an external source of compression is applied to stress the target body, it may be generally assumed that the volumetric strain (or differential displacement) along the axis of compression may be determined by the formula:

$$\text{strain} = (\Delta L/L) \qquad \text{Equation 2}$$

where $\Delta L$ = a change in the length of the segment along the axis of compression, and L = the original length of the segment, Further, it may be generally assumed that the stress on the tissue segment of interest caused by the external source of compression may be determined by the formula:

$$\text{stress} = (F/a) \qquad \text{Equation 3}$$

where

F = compressive force applied to the segment, and a=area across which the force is applied.

Therefore, applying these assumptions to Equation 1, the elastic modulus (E) of a tissue segment of interest may be estimated by the formula for determination of a Young's modulus:

$$E=(F/a)/(\Delta L/L) \quad \text{Equation 4}$$

Further, compressibility (K), the inverse of E, may be estimated by the formula:

$$K=(\Delta L/L)/(F/a) \quad \text{Equation 5}$$

Thus, the compressibility of any given segment or layer within a material relative to another segment or layer may be further estimated from the relationship $$K_1=K_2\,(\Delta L_1/L_1)/(\Delta L_2/L_2) \quad \text{Equation 6}$$

where $K_1$=compressibility of a first segment or layer;

$\Delta L_1$=change in length of the first segment or layer along an axis of compression in response to a given force;

$L_1$=original length of the first segment;

$\Delta L_2$=corresponding change in length of a second segment or layer;

$L_2$=original length of the second segment or layer; and $K_2$=compressibility of the second segment or layer.

In elastography, the velocities of sound in different segments or layers may be employed, together with time measurements, to calculate distances within the segments or layers. The ultrasonic signals also provide a precise measuring tool. The velocities of sound may be determined using the apparatus and procedures disclosed in application Ser. No. 7/438,695.

However, in the techniques previously disclosed for elastography in applications Ser. Nos. 7/438,695 and 7/535,312, the method for estimating compressibility in targets having multiple layers may lead to some inaccuracies. These inaccuracies may similarly arise in sonography. Such inaccuracies generally result from one of two conditions, or both. Thus, a first group of such inaccuracies may arise due to substantial variations in the speed of sound in the different layers. Expressed otherwise, the techniques estimate compressibility in each layer from two echo sequences along the axis of radiation without consideration for variations in the speed of sound.

Some regions in a target body of interest may contain multiple layers having substantially different velocities of sound. For example, the human body wall may include regions of interspersed fat and muscle tissue, and sound may typically travel at about 1450 m/s in a fatty region, while it will typically travel faster in muscle tissue, around 1580 m/s. The variation in the speed of sound through different layers can cause sonic pulses traveling on different sonic paths, but through the same distance relative to the transducer, to take different amounts of time. This time difference may in turn lead to a distortion, and possibly a shift, in the elastograms and sonograms of the target body.

A second condition that may cause a significant inaccuracy in the previously disclosed techniques for elastography lies in the assumption that stress will be relatively uniform throughout the tissue of interest, and may be calculated for all layers based on measurements proximal to the compressor. However, inaccuracies have been observed if the transducer and compressor used to compress and sound a tissue are relatively small in area relative to the depth (or thickness) of the target body, giving rise to decreasing stress in the target body as the distance increases from the compressor. If this decreasing stress is substantial and unaccounted for, levels of decreasing compressibility may appear on the elastograms as a function of increasing distance from the compressor.

Thus, the present invention in one aspect provides a method and apparatus to determine the strain and compressibility of a target body regardless of whether the target body has multiple layers with different sonic velocities. In another aspect, the invention provides a method and apparatus to determine the compressibility of a target body even where the stress in the target body resulting from compression by the compressor decreases with distance from the compressor. In yet another aspect, the invention generally provides an ultrasound method and apparatus for accurately measuring and imaging strain and elastic modulus distributions in an elastic tissue. The ability of the invention to quantitatively measure the compressibility or compliance of tissue in localized regions provides help with (1) objective quantification of commonly used clinical signs, (2) localizing these measures, (3) making the measurements deep in tissue with simple equipment, (4) observing new tissue properties, which may be related to pathology, not seen by other known means; and (5) constructing images of a compressibility or compliance parameter in vivo, which may be used alone or in conjunction with ordinary sonograms. Diseased tissue, such as tumors, may be harder or softer than normal tissue, and thus have a different amount of compressibility. In this regard, elastography gives promise of a distinct advantage over prior art methods in the accurate detection of diseases such as breast cancer and prostate cancer and localization of tumors at an early stage. Another advantage of elastography is that its sensitivity may be greater than sonography, because of its measurement and imaging of compressibility and not just echo amplitudes, allowing for better visualization of target bodies. Still another advantage of elastography is the accurate imaging of sub-surface tissue while avoiding the use of ionizing radiation from x-rays.

It will be noted at this point that elastography is contemplated to have significant applications other than in medicine. One such application, for example, is in the quality grading of beef. Elastography may be used to quantitate both the tenderness of beef and the fat content (marbeling) before and after slaughter. This ability is economically important in determining when to slaughter cattle. Other applications may include, for example, interrogation of materials and products such as cheese or crude oil that are physically displaceable by the movement of a transducer. Other objects and advantages of elastography will become readily apparent from the ensuing description.

In a broad sense the present invention comprises an ultrasonic system for producing improved elastograms and sonograms of elastic target bodies, and notably animal and human tissue. In one broad aspect, elastography comprises sonically coupling a sonic device to a target body to determine its compressibility. The sonic device is used to emit an ultrasonic signal and receive returning echo sequences from along a sonic path in the target body. The sonic device is then moved a known amount along the axis of the sonic path, and the target body is interrogated again along the sonic path. Congruent segments in echo sequences from the different sonic signals are then preferably cross correlated or matched, and the temporal displacements are used to calculate the strain along the sonic path. This procedure is repeated for a plurality of sonic paths, either sequentially or by means of a sonic array, to produce strain profiles for the target body.

To obtain a compressibility profile, a second body having a known, preferably uniform, elastic modulus may be first sonically joined to and between the target body and the sonic device. The strain profiles of both bodies may then be determined using the steps described above. The stress caused by the movement of the sonic device may then be determined from the strain profiles and elastic modulus of the second body. Compressibility profiles for the target body may be obtained by dividing the values for the strain profiles in the target body by the stress. The resulting compressibilities may be further arranged as an elastogram, a positional multi-dimensional plot or picture of the relative magnitudes of compressibility of a tissue or other target body.

In another aspect, the invention resides in using the above method of elastography, but further correcting for variations in stress along the sonic path. These variations may occur in instances where a sonic device, which is employed to stress and compress the target body, has a small cross-sectional area relative to the depth or thickness of the target body. These variations in stress may be determined by first measuring the dimensions of the surface of the sonic device (which may include a transducer in combination with a compressor) which contacts the second body. These measured dimensions may then be applied to analytically derive the variations in stress within the target body as a function of position relative to the sonic device. The result is, in effect, a stress profile. Once derived, these variations in stress may be applied to correct the values for the stress profiles, as well as the resulting compressibility profiles and elastograms for the target body, previously determined by use of the above-described preceding embodiment.

In another aspect, the above variations in stress may be experimentally derived. Thus, a body of known elasticity may be compressed by the sonic device and the resulting strains along varying sonic paths inside the body may be measured. The variations in stress may then be calculated as a function of position relative to the sonic device. From these known variations the corrected values for the stress and compressibility profiles and elastograms may then be determined.

In yet another aspect of the invention, appropriate time delays, necessary to correct for variations in echo sequence travel time through regions of the target body having different speeds of sound, may be determined and applied to each echo sequence. The resulting time shifts in echo sequences correct for distortions that might otherwise occur when there are different regions within a target body, e.g., fat and muscle tissue, that have differing sonic velocities.

In yet another aspect of the invention, the dynamic range over which elastographic measurements are taken is increased over prior elastographic techniques. The range of elasticities of tissue regions over which accurate elastographic measurements can be taken is referred to as the "dynamic range." In prior art elastographic techniques, this dynamic range is approximately 10/1. That ratio represents the range of elasticities of the tissue regions that can be accurately measured.

In certain applications, the target body is a heterogeneous volume of tissue, such as a breast. Such a tissue body may contain fat, fibrous tissue, and possibly tumorous tissue. The range of elasticities encompassed by these regions or structures is typically several orders of magnitude. The fat is soft tissue while the tumor is hard tissue. When such a heterogeneous tissue body is compressed, the soft tissue will compress much more than the hard tissue. This can result in undetectable compression in the hard tissue and large, distorted compression in the soft tissue or fat.

When a heterogeneous tissue body is initially compressed a small amount, the resulting strain in the hard tissue region is virtually undetectable. This undetectability can be evidenced by a cross-correlation analysis that shows a zero strain readings in the hard tissue regions. Thus, at low levels of compression, soft tissue regions in a heterogeneous body may yield good strain readings while at higher levels of compression, hard tissue regions in a heterogeneous body may yield good strain readings. As the degree of compressive stress is increased, the soft tissue regions will produce distorted cross-correlation readings, which will, in turn, produce erroneous strain estimates.

The present invention provides a method and apparatus for measuring the strain of all tissue regions within such a heterogeneous tissue body without degradation. This is accomplished by initially measuring the displacement along a force axis in a heterogeneous tissue body and then by compressing or decompressing the tissue in multiple steps, or units of compression, measuring the displacement and then estimating the strain based upon the differential displacement of two successive ultrasound pulses. The estimation of differential displacement can be accomplished using a number of analytical methods well known in the art, including a cross-correlation technique, a phase of the cross-spectrum technique, or a phase of the analytic signal technique.

Based upon the results of the comparison, a decision is made as to which tissue regions along the force axis have yielded "good" strain data. Strain data which is subjectively evaluated to be good strain data is stored in a retrievable data storage medium. The process is repeated until good strain data is obtained along the desired length of the force axis. This multiple step compression sequence is continued until a total compression or decompression, displacement or stroke, h, is achieved.

Compression is typically accomplished by pressing an ultrasonic transducer against the tissue body in multiple compression increments. Compression can also be accomplished by pressing an object, other than the transducer, against the surface of the target body, applying a compressive force to a surface of the target body opposite the surface where the transducer is sonically coupled, or projecting sonic waves with sufficient intensity toward the target body to result in displacement of the target body surface.

The transducer is then retracted in steps from the tissue body to reverse the compression process along the total compression displacement h. During the retraction or decompression process, strain measurements are taken for each step.

This reciprocating compression/decompression method is known as an oscillatory method. This method is advantageous because it maximizes the number of measurements obtained per compression cycle, thereby improving the quality of data and enabling the user of the invention to analyze any hysteresis in the target body under interrogation.

This aspect of the invention allows accurate analysis or following of the compression in soft tissues areas while effecting a large total displacement, as required, in order to detect any compression in harder tissue regions. The end result is that the dynamic range of the elastogram is increased by at least one order of magnitude.

In another aspect of the present invention, an apparatus is provided for practicing the compression/decompression method described above. This apparatus provides a shaft driver device coupled to one end of a shaft whose other end is coupled to an ultrasonic transducer or transducer array.

The shaft driver device is capable of extending and retracting the shaft and transducer in preselected displacement increments at preselected speeds. A shaft displacement controller is further provided for adjusting the amplitude or magnitude of the displacement increment that the shaft driver device extends or retracts the shaft and transducer in response to an input selection. A shaft speed controller is also provided for adjusting the speed or frequency at which the shaft and transducer are moved by the shaft driver device in response to an input selection.

In another aspect of the present invention, a method is provided for interrogating target bodies accessible only through body cavities, such as the prostate gland. In this application, a transducer is inserted into a body cavity, such as the rectum, and a coupling device is inflated in the free space between the transducer and the target body so as to cause the increments of compression and decompression necessary to practice the reciprocating method, described herein.

BRIEF DESCRIPTION OF THE DRAWINGS

The present invention, together with further advantages and features thereof, may be more readily understood by reference to the following detailed description taken in connection with the accompanying drawings in which:

FIG. 1b shows a plot of an RF echo signal originating from the distal tissue region interrogated in FIG. 1a.

FIG. 2b shows a plot of a typical pre- and post-compression RF echo signal pair originating from the distal tissue region as interrogated in FIG. 2a.

FIG. 5b shows a B-scan of the phantom pictured in FIG. 5a.

FIG. 5c shows the elastogram corresponding to the B-scan shown in FIG. 5b.

FIG. 5d shows the depth-corrected elastogram corresponding to the B-scan shown in FIG. 5b.

DETAILED DESCRIPTION

Figure 1A:
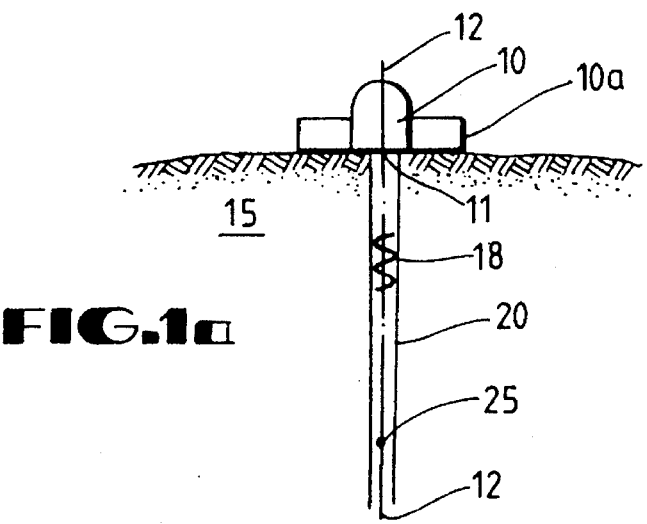
FIG. 1a shows an embodiment of an elastographic apparatus where a transducer and compressor are sonically coupled to a target body to interrogate a distal tissue region within the target body.

FIG. 1a shows the transducer 10 and compressor 10a sonically coupled to a target body 15. An ultrasonic pulse 18 is shown propagating within sonic beam 20 toward an echo source 25 on beam axis 12. As the pulse 18 propagates through the target 15, corresponding echoes are generated and arrival times noted at the transducer aperture 11. The combination of all echoes generated from reflections within the beam 20 is the echo sequence or A-line corresponding to pulse 18.

Figure 1B:
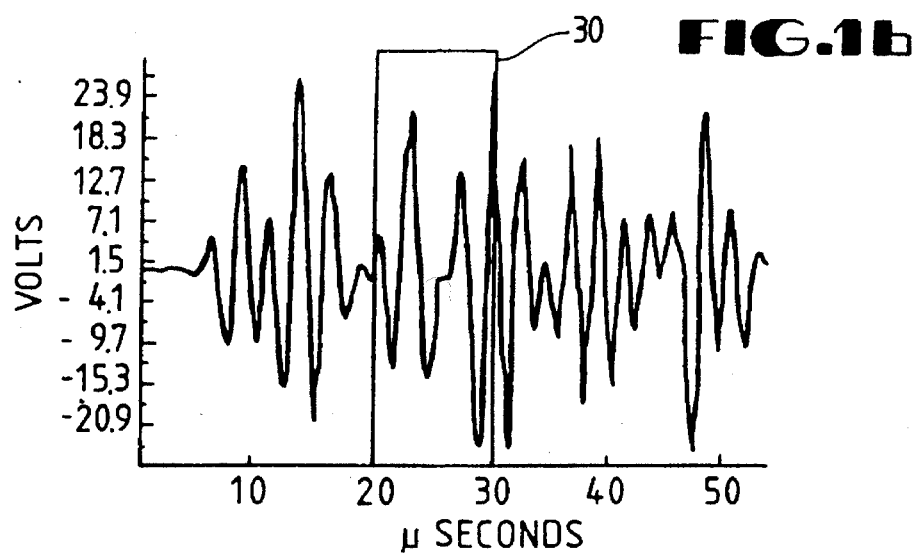

A radio frequency ("RF") signal plot of the A-line acquired from pulse 18 is shown in FIG. 1b. The amplitude of the signal in volts is plotted against echo arrival times in microseconds (µs). Later arrival times correspond to progressively deeper regions within the target body 15. An echo segment or echo wavelet 30, within a chosen arrival time window, is selected as a reference. The time window may be selected based on anatomical data from ultrasound imaging, or may be arbitrary, e.g., every x micro seconds. The echo segment or wavelet 30 originates from the echo source 25.

Figure 2A:
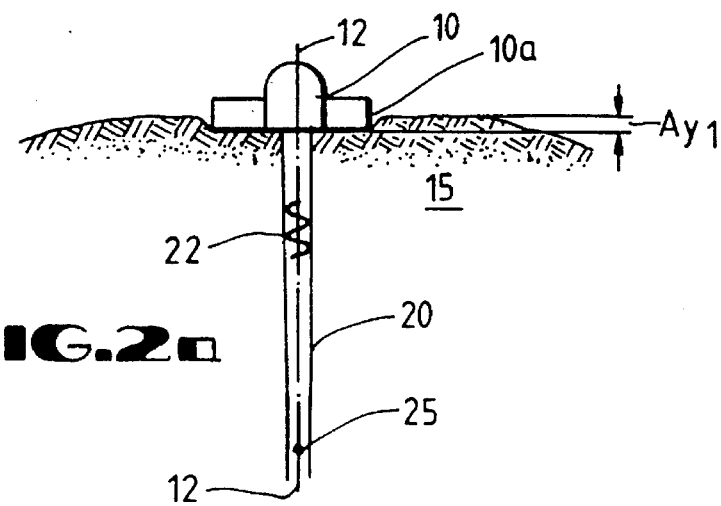
FIG. 2a shows the transducer and compressor of FIG. 1a imparting a small compression to a proximal region of the target body.

FIG. 2a shows the transducer 10 and compressor 10a being translated along axis 12 to impart a small compression ($\Delta y_1$) to the tissue. After the transducer 10 and compressor 10a compress the target body 15, a second pulse 22 is emitted and the corresponding A-line segment is acquired from a desired depth within the tissue.

Figure 2B:
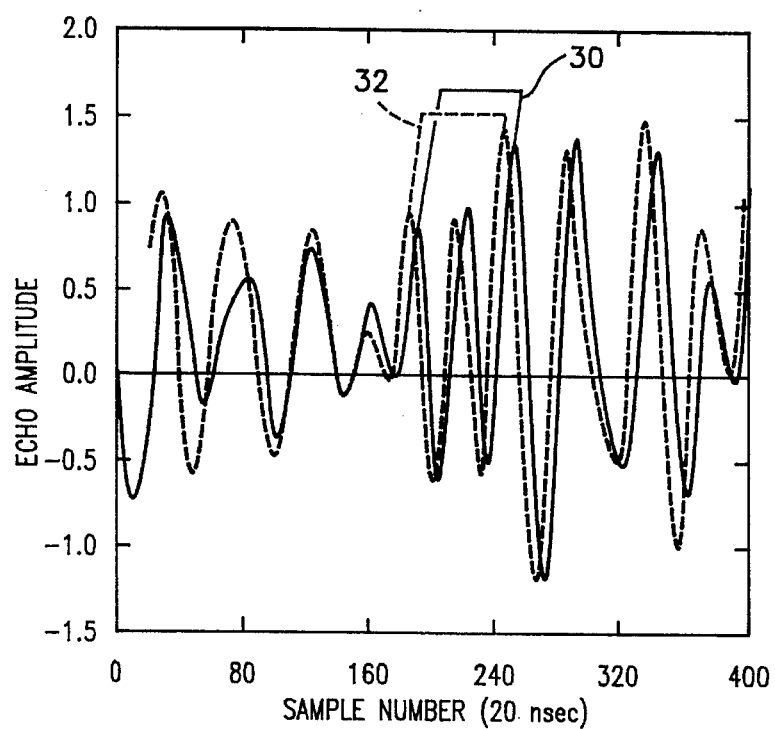

FIG. 2b shows an RF plot pairing a typical pre-compression A-line, corresponding to pulse 18, and a post-compression A-line, corresponding to pulse 22. The echo segment or wavelet 32 associated with a given echo source and pulse 22 is time shifted with respect to the same segment of wavelet 30 associated with the same echo source and pre-compression pulse 18. The time shifted wavelet 32 may be tracked within the selected time window using standard pattern matching techniques. The window selected must be such that the wavelet of interest will not be shifted out of the window. This selection may involve the size of the window or the positioning of the window. The window selected should reveal both wavelets or echo segments. The arrival time of echo segment or wavelet 32 is prior to that of echo segment or wavelet 30 above, since the distance between aperture 11 and feature 25 was shortened by the compression $\Delta y_1$.

Figure 2C:
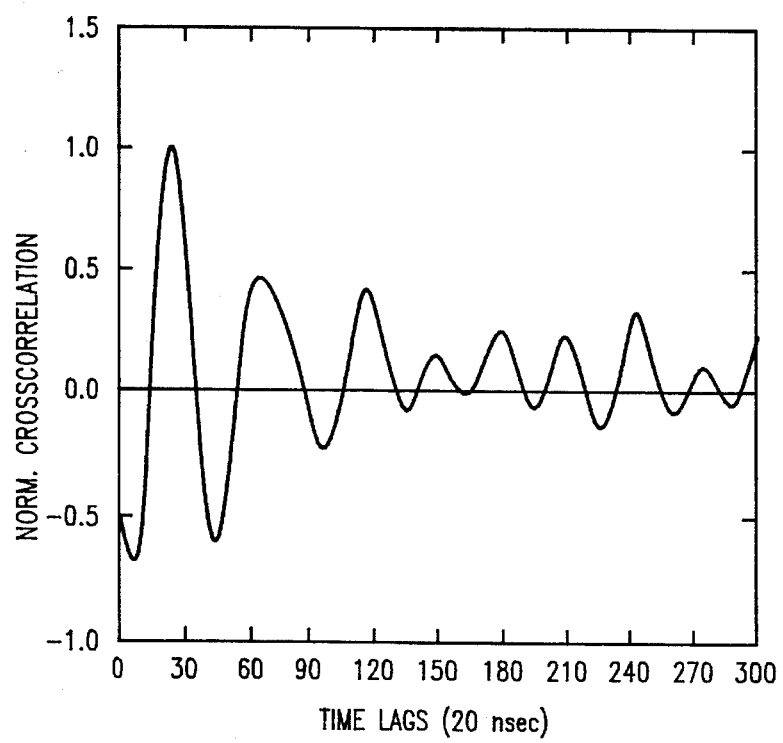
FIG. 2c shows a plot of a cross correlation of the echo signal pair shown in FIG. 2b.

FIG. 2c shows the cross-correlation function between the pre- and post-compression A-lines shown in FIG. 2b.

In a preferred method of elastography, a transducer and compressor are positioned on or otherwise coupled to a target tissue and advanced axially toward the target to compress the target. Alternatively, elastography may be practiced by retracting a transducer and compressor from a previously compressed position. Further, in both methods the transducer may alone serve as the compressor. Since the relatively large size of the compressor precludes penetration of the tissue, small tissue displacements occur instead. A pulse is emitted from the transducer prior to the displacement, and a first echo sequence received in response to the pulse is recorded. Following displacement, a second pulse is emitted and a second echo sequence is recorded in response to transmission. Next, a comparison of the waveforms is made to reveal a decreasing displacement of the tissue structure with depth. The decrease will generally be asymptotic in character.

In the foregoing method, a single compression of a homogenous target body has been described. It will be apparent, however, that other conditions may be employed. Thus, multiple compressions, repetitive or real time compressions, varying waveforms and other signal sources, such as array transducers, may be used. These signal sources, for example may be non-repetitive and may generate spike-like signals.

Further, an internal source of compression, alone or in conjunction with an external compressor, may be used. In the case of an internal source of compression, such as the heart or arteries, the tissue of interest should preferably be located sufficiently distant from the internal source of compression such that stress caused by the internal source of compression, even while changing as a function of time, remains substantially uniform throughout the tissue of interest. A transducer may then be sonically coupled to the target body, preferably with a compliant body of known uniform elasticity sonically coupled between the transducer and the target body, such that the tissue adjacent to the transducer compresses against the compliant body and transducer as the tissue is compressed by the internal source of compression, and decreases in stress against the transducer and compliant body as the stress caused by internal source of compression decreases in the tissue of interest. The strain in the compliant body and tissue of interest may then be sonically measured using the method described herein, and the stress against the compliant body determined from elasticity and strain measurements for the compliant body. Finally, this stress may be assumed to be the level of stress throughout the tissue of interest, and used with the measured strains to determine the compressibility profile in the tissue of interest.

In tissue that is not homogeneous, the shifting of tissue in various segments will differ. For example, if a segment of tissue is less compressible than the overall tissue containing the segment, the tissue in the segment will compress or strain less than if the segment of tissue were of the same compressibility as the tissue as a whole. Alternatively, when a segment is more compressible than the tissue as a whole, the segment will compress or strain more than if the segment were of the same compressibility as other segments. The presence of a strain "defect," or segment of different compressibility, along the compression axis in a target body influences all other strains along that axis, increasing or decreasing the otherwise proportional change in strain with depth along the axis. In this way a strain "defect" is said to be "smeared" along the axis. For this reason, it may be preferable to convert the strain profiles into elastic modulus profiles. Since the elastic modulus is a basic tissue property, it may be ultimately a more reliable parameter. In any event, it is possible to obtain useful images from strain or elastic modulus data.

In order to illustrate these principles, it is convenient to consider a simple one-dimensional cascaded spring system, where the spring constants represent the elastic moduli of tissue regions. We assume that all three springs are equal and are of length l, and that each spring represents the behavior of a cylindrical tissue element with unit cross section. If the top of the first tissue element is compressed by an axial downward force such that the overall length of the system is reduced by ($2\Delta y$), then a simple statics calculation shows that each and every spring will shrink by $\Delta l=2\Delta y/3$. If we define the strain of each spring=$\Delta l/l$, it is clear then that the strain is constant for all springs, and is equal to $2\Delta y/3l$.

Where the center spring has been replaced by an infinitely stiff spring, i.e. $E=\infty$, the total displacement is taken up by two outer springs only. Thus, the strain in the two outer springs will increase to $\Delta y/l$.

It is evident from this example that a strain profile is dependent on the initial compression and on the number and stiffness of all springs. A given local measured value of the strain is influenced by the elastic properties of elements located elsewhere along the axis of compression. For these reasons, it appears that while strain profiling may be useful for imaging, it may be of limited use for quantitative estimation of local tissue elasticity.

If instead of imparting a known displacement a known stress is applied, it becomes possible to estimate the elastic modulus of each component in this system of springs, since the stress remains constant with depth in this one dimensional system. In this case, the measurable strain in each spring and the known stress on each spring may be used to construct an elastic modulus profile along the compression axis. Such a profile would be independent of the initial compression, and the interdependence among the component springs would disappear.

Further, the stress applied to the target body may be measured ultrasonically by interposing an anterior compliant standoff layer which has a known value of E, and which allows the free passage of ultrasonic waves. The simultaneous measurement of the strain in this layer allows the computation of the stress acting on the target. This layer may consist of compressible or compliant material such as rubber, sponge, gels, etc. The material should be compressible and provide for an ultrasonic transmission path to the tissue. The material may be echogenic, but it is not necessary.

In the more realistic three-dimensional case, one would expect that the applied stress would not be constant along the axis of compression. The reason for this lies in the fact that stresses along transverse springs become important, and since their vertical force components are a function of the displacement which in turn is a function of depth, the resultant forces along the compression axis vary with depth. On the other hand, enlarging the area of the compressor, the transverse springs that are actually stretched, and hence contribute to the depth dependent stress field, become less important and the applied stress field becomes more uniform. Experiments have confirmed that larger compressors cause more uniform axial stress fields.

In elastography, however, the velocities of sound in different segments or layers are used, together with time measurements, to calculate distances within the target body. More specifically, elastograms are based on time shift differences among segments of ultrasound A-lines and preferably, when based on more than about 64 data points, rely heavily on cross-correlation computations. The use of cross-correlation analysis for time shift estimation derives from Fourier theory, and is well known in the art. In recent years a number of industrial and medical applications have utilized cross-correlation analysis for time shift measurements. The application of ultrasonic correlation techniques to the measurement of flow velocity of coal slurries has been described. Similarly, an ultrasonic correlation flowmeter for pulp suspension has been proposed. In the medical field, a number of publications describe the measurement of blood velocity profiles using one-dimensional and two-dimensional correlators, as well as applications of cross-correlation measurements for tissue motion evaluations, described above.

The generation of an elastogram involves a pairwise evaluation of the time shift between congruent segments in an A-line pair, preferably by means of cross-correlation techniques. The linear cross-correlation of segment pairs may be computed using FFTs (fast Fourier transforms). The temporal location of the maximum peak of the cross-correlation function may be used to estimate the time shift between the data in the two segments.

However, the time shift differences among segments of an ultrasound A-line may also be evaluated by using a least-means-square match analysis, which is also well known in the art, or by manually measuring the differences between A-lines on a display or picture, instead of by cross-correlation. When there are less than about 64 data points being analyzed, a time domain computation, such as a least-means-square match, may often take less time than a fourier domain cross-correlation computation will take to determine the time shifts. Further, a least-means-square match analysis may be computed for a limited number of time-lags, where the approximate time shift is known, while cross-correlation using an FFT computation must analyze the entire data sequence. Thus, a least-means-square match may be faster than cross-correlation where the approximate time-shift is known, allowing a time-shift determination to be made by matching only a portion of the echo sequences.

By way of illustration only, one approach to elastography could involve the derivation of an elastogram from a strain image created from 40–60 A-line pairs obtained with a 1–2 mm lateral translation of the transducer between pairs. An A-line pair consists of the original A-line which is obtained with the transducer slightly pre-compressing the target in order to assure good contact, and a compressed A-line which is obtained after axially compressing the target an additional $\Delta z$. The compressed A-line would be shorter than the original A-line by $2\Delta z/c$, where c is the speed of sound in the target. The length of the A-line pair is taken to be that of the original A-line; zeros are appended to the compressed A-line. These A-lines would be obtained from a 12 cm total depth in the target, and divided into 40–60 overlapping 4 mm segments obtained every one or two mm.

The data acquisition, and therefore the time scale, is relative to the face of the transducer. Thus one can observe that the relative shift of the signal at the beginning of an A-line pair is very small, whereas towards the end it is significant. In general, the time shift of the compressed A-line relative to the uncompressed A-line would increase from 0 to a maximum of $2\Delta z/C$.

In general, the precision of the time shift estimate improves with increasing segment size. However, it is typically better to keep the segment size small to improve the axial resolution of the estimate. Additionally, because of the relative compression and the resultant progressive distortion of the data within a segment pair, the cross-correlation estimate may deteriorate with increasing segment size. This, in turn may degrade the precision of the estimate. Thus, there are two competing mechanisms that affect the precision of a time shift estimate as a function of the segment size. Although this trade-off has not been studied in depth, it has been observed that a segment size of about 4 mm with about 3 mm overlap between segments leads to strain data which may result in reasonable images with about 1 mm axial resolution.

The resolution of a measured time shift may be bounded by the sampling period at which the data is digitized. To improve the resolution, some interpolation algorithms have been proposed. For example, a quadratic interpolation algorithm has been shown to be effective and it is simple to implement. See, Foster et al., "Flow Velocity Profile Via Time-Domain Correlation," IEEE Trans. Ultrason. Ferroel. Freq. Control, Vol. 37, No. 2, 164–174 (1990); See also, Boucher et al., "A Method of Discrete Implementation of Generalized Cross-Correlator," IEEE Transactions: Acoustics, Speech and Signal Processing, Vol. ASSP-29, No. 3 (June 1981). This algorithm first fits a second-order polynomial which passes through the peak sample value of the cross correlation and its two neighbors using the Lagrange polynomial interpolation. Then it analytically locates the peak of the fitted polynomial, assigning that temporal value to the improved time shift estimate.

Returning to the illustration, after processing one A-line pair a set of time shifts, t1 through t60, may be obtained. The corresponding strain profile may then be defined by the relationship $$S_i = \frac{t_{i+1} - t_i}{2\Delta x/c} \; ; i = 1 \text{ to } 59 \qquad \text{Equation 7}$$

where $s_i$ is the strain estimate for segment pair i, and where $\Delta x$ is an axial increment.

The process may then be repeated for all A-line pairs, resulting in an array of strain data. These values may then be scaled and assigned to an intensity for display, e.g., an intensity varying within 256 grey scale levels. Due to the large dynamic range of some strain data, contrast stretching may be applied in order to observe variation in particular strain ranges. For example, 256 grey scale levels may be assigned to a user specified strain range, thus stretching the contrast in that region.

In general, elastography contemplates sonically coupling an ultrasonic source to a target body; energizing the ultrasonic source to emit a first ultrasonic signal or pulse of ultrasonic energy from the source along an axis into the target body; detecting from a region within the target body a first echo sequence including a plurality of echo segments resulting from the first transmitted signal; displacing the target body along the axis while maintaining coupling between the ultrasonic source and the target body; energizing the ultrasonic source to emit a second ultrasonic signal along the axis into the target body; and detecting from the region within the target body a second echo sequence including a plurality of echo segments resulting from the second transmitted signal; and measuring the differential displacement of the echo segments. A plurality of first ultrasonic signals or pulses of ultrasonic energy may be emitted and a plurality of first echo sequences detected before compressing the target body. Then a plurality of second signals and pulses are emitted along a plurality of parallel paths and a plurality of second echo sequences are detected.

In one embodiment of elastography, a transducer is the ultrasonic source and is sonically coupled to direct an ultrasonic signal or pulse of ultrasonic energy into the tissue along a radiation axis such that movement of the transducer along the axis effects a change in compression of the tissue.

In a preferred embodiment of elastography, the ultrasonic source is a transducer sonically coupled to a tissue of interest. A first pulse of ultrasonic energy is emitted along a path into the target body and the arrival of a first echo sequence (A-line) including one or more echo segments is detected from regions within the tissue along the path resulting from the first pulse of ultrasonic energy. Thereafter, compression is changed within the tissue along the path. The compression change may be accomplished by transaxially moving the transducer along the path to compress or displace a proximal region of the tissue. A second pulse is emitted, and the arrival of a second echo sequence including one or more echo segments common to the first echo sequence is detected in response to the second pulse. The differential displacements of at least one echo segment are measured. The echo sequences detected are from common regions within the tissue.

A comparison of the first and second echo sequences or waveforms with intervening compression reveals a generally decreasing displacement of tissue structures with depth. In a homogeneous medium, the rate of decrease will tend to be asymptotic. Of particular interest is the differential displacement per unit length—i.e., strain. In a homogeneous compressible medium, the strain will tend to be constant along the axis of compression.

In a non-homogeneous medium, the strain varies along the axis of compression.

The strain of a tissue may be calculated using the arrival times of first and second echo sequences from proximal and distal features in a target body—i.e., tissue—using the following equation:

$$\frac{(t_{1B} - t_{1A}) - (t_{2B} - t_{2A})}{(t_{1B} - t_{1A})} \qquad \text{Equation 8}$$

$t_{1A}$=arrival time of a first echo sequence from a proximal feature;

$t_{1B}$=arrival time of a first echo sequence from a distal feature;

$t_{2A}$=arrival time of a second echo sequence from a proximal feature; and $t_{2B}$=arrival time of a second echo sequence from a distal feature.

The arrival times of the echo segments from a common point detected in response to a first and second pulse of ultrasonic energy are compared. The common points may be found in features occurring within the echo signal. The time shifting of the two echo segments is used to determine compressibility.

Thus, if no change in arrival time has occurred with an intervening compressive force, it follows that a target body has not been compressed along the travel path leading to the source of the echo segments. On the other hand, if the arrival time of the second echo segment is smaller than the arrival time of the first echo segment, it is clear that compression has occurred and that the target body is compressible. Moreover, the difference in arrival times, taken together with other available data, makes it possible to quantify the compressibility of the target body.

In another embodiment of elastography, body segments which extend along the transmission path of the ultrasonic pulses are selected within a target body and separate first and second echo segments detected from within each body segment. Thus, a series of first and second echo segments is detected for the body segments selected for interrogation. Preferably, the echo segments are detected from the proximal and distal ends of body segments relative to the ultrasonic source. Measurement of the time shifts of echo segments in the first and second echo sequences which correspond to the proximal and distal ends of each body segment are then made. By studying the time shifts, it becomes possible to determine whether changes in compressibility occur along the ultrasonic beam within the target body.

A preferred embodiment of elastography involves (1) sonically coupling a material with a known Elastic Modulus and speed of sound to the surface of the target body; (2) emitting a first pulse of ultrasonic energy along a path through the material into the target body; (3) detecting a first echo sequence including a plurality of echo segments, from within the target body resulting from the first pulse; (4) forcing the material against the target body sufficiently to displace the target body while maintaining acoustic coupling between the material and the target body; (5) emitting a second pulse of ultrasonic energy along the path through the material into the target body; and (6) detecting a second echo sequence including a plurality of echo segments common to the first echo sequence, resulting from the second pulse. The presence of the material with a known Young's modulus and speed of sound makes it possible to determine the Young's modulus of the target body. If the target body, itself, has multiple layers, it also becomes possible to determine the Young's moduli of the individual layers. The application of Young's modulus to these matters is explained later in this description.

At this point it is worth noting that elastography takes advantage of the acoustical properties of physically compressible or displaceable materials. These materials—for example, animal or human tissues—often contain a large number of acoustic "scatterers". The scatterers, being small compared to the wavelength of the sound frequencies involved, tend to reflect incident sound energy in all directions. For example, in homogeneous tissue regions, scatterers may comprise a collection of nearly identical reticulated cells. A particular arrangement of scatterers will shift in response to axial forces from the transducer, changing the time an echo is received from the arrangement. The echoes received from the various arrangements of scatterers form an echo sequence. A selected echo segment or wavelet of the reflected RF signal corresponds to a particular echo source within the tissue along the beam axis of the transducer. Time shifts in the echo segment or wavelet are examined to measure compressibilities of tissue regions. It is important that the shape of the echo segment or wavelet not change significantly, due to compression, such that identification of the wavelet is not possible, and that the signals not be decorrelated beyond an acceptable range. The time shift can be determined by analyzing the data in a computer or by a visual examination, but the analysis will generally be easier with a computer.

Studying an internal region of the human body is accomplished by sonically coupling an ultrasonic transducer to the body so as to emit an ultrasonic signal along an axis into the region, and such that movement of the transducer along the axis relative to the region will change the compression of the body between the transducer and the region; energizing the transducer to emit a first signal along the axis into the body and the region; detecting the arrival at the transducer of a plurality of spaced echo segments resulting from the first signal and coming from the region; moving the transducer along the axis relative to the region sufficient to change the compression of the body between the transducer and the region while maintaining said sonic coupling; energizing the transducer to emit a second signal along the axis into the body and said region; detecting the arrival at the transducer of each echo segment resulting from the second signal; and determining the strains produced in segments of the region between the pairs of echo segments.

Elastography is of particular interest in interrogating organic tissue, especially human and other animal tissue. Thus, as a transducer is pressed against such a material, scatterers in a region within the material are displaced from one position to another. For elastic materials, release of the pressure enables the scatterers to return to their original position. A principal object of such interrogation is to use echo signals from the tissue in strain studies which may reveal the presence of abnormalities. In general, when employing a transducer to transmit signals into a living body, care should be taken to coordinate the transducer sound signals with naturally occurring movements. Thus, in the human body, the transducer should normally be activated at times which will minimize interference by movements of structures such as the pumping of the heart or pulsation of an artery. It should be noted, however, that it may be possible to use such movements, where the stress and strain resulting from such movements may be determined, either in place of or in conjunction with an external source of compression, in the practice of elastography and of the invention.

It will be noted that the transducers employed in elastography need not be in direct contact with the materials to which they are applied. It is necessary, however, that transducers be sonically coupled to the materials in a manner such that movement of the transducers will result in displacement of the materials. Sonic coupling methods and agents are well known in the art.

It will be also noted that a material may be displaced according to elastography either (a) by advancing a transducer against a compressible elastic material to increase compression, or (b) by retracting a transducer from a compressed position within the material. Changing compression means compressing or decompressing the target body.

As noted above, it is not necessary that an echo from a discrete feature in a tissue or other compressible material be employed. It is sufficient that an identifiable echo segment be present in the echo signal resulting from a transmittal signal. Even though the physical features within a material responsible for a selected echo segment may not be clearly known, the selected echo segment is an adequate reference for the purposes of elastography. Thus, the compression of a material and signal travel times determined before and after such compression may be based upon comparison of time shifts in the echo segments. Similarly, the recovery of an elastic material from an initially compressed condition and the signal travel times before and after such recovery or decompression may be based upon comparisons of time shifts in the echo segment.

Elastography may also be employed for estimating compressibility or compliance in targets having multiple layers. It will be noted that the terms "compressibility" and "compliance" in the present context have generally similar connotations. In any event, the compressibility in each of the progressively deeper layers is estimated by employing the same techniques discussed above. For example, the compressibility may be estimated in each layer from only two echo sequences along the axis of radiation. The echo sequence may be divided into echo segments corresponding to the layers. Thus, imaging of the compressibility parameter in a plane or volume of a target body may also be accomplished by appropriate lateral translation of the transducers.

Figure 3A:
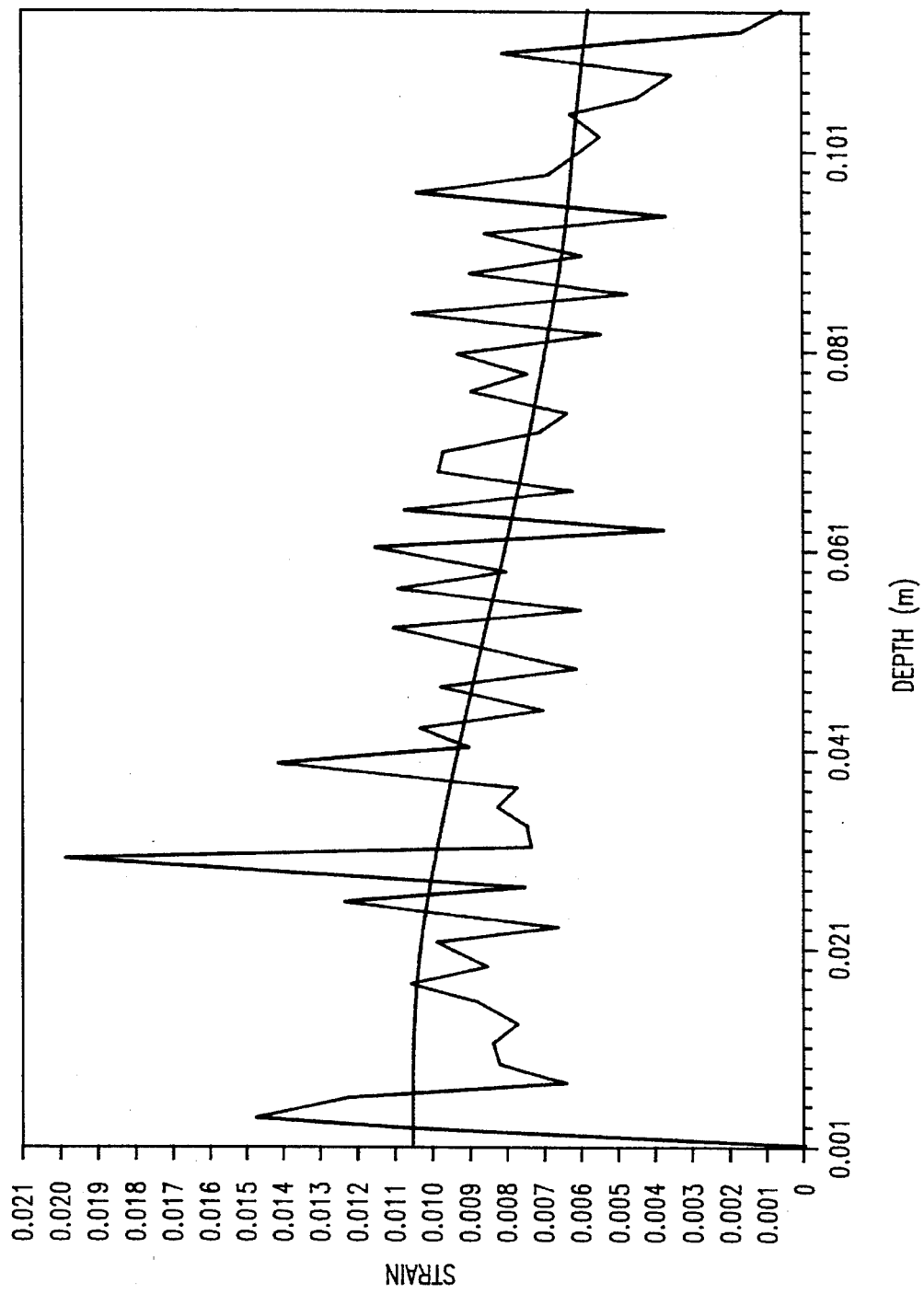
FIG. 3a shows the axial strain in foam as a function of depth using a 127 mm circular compressor.
Figure 3B:
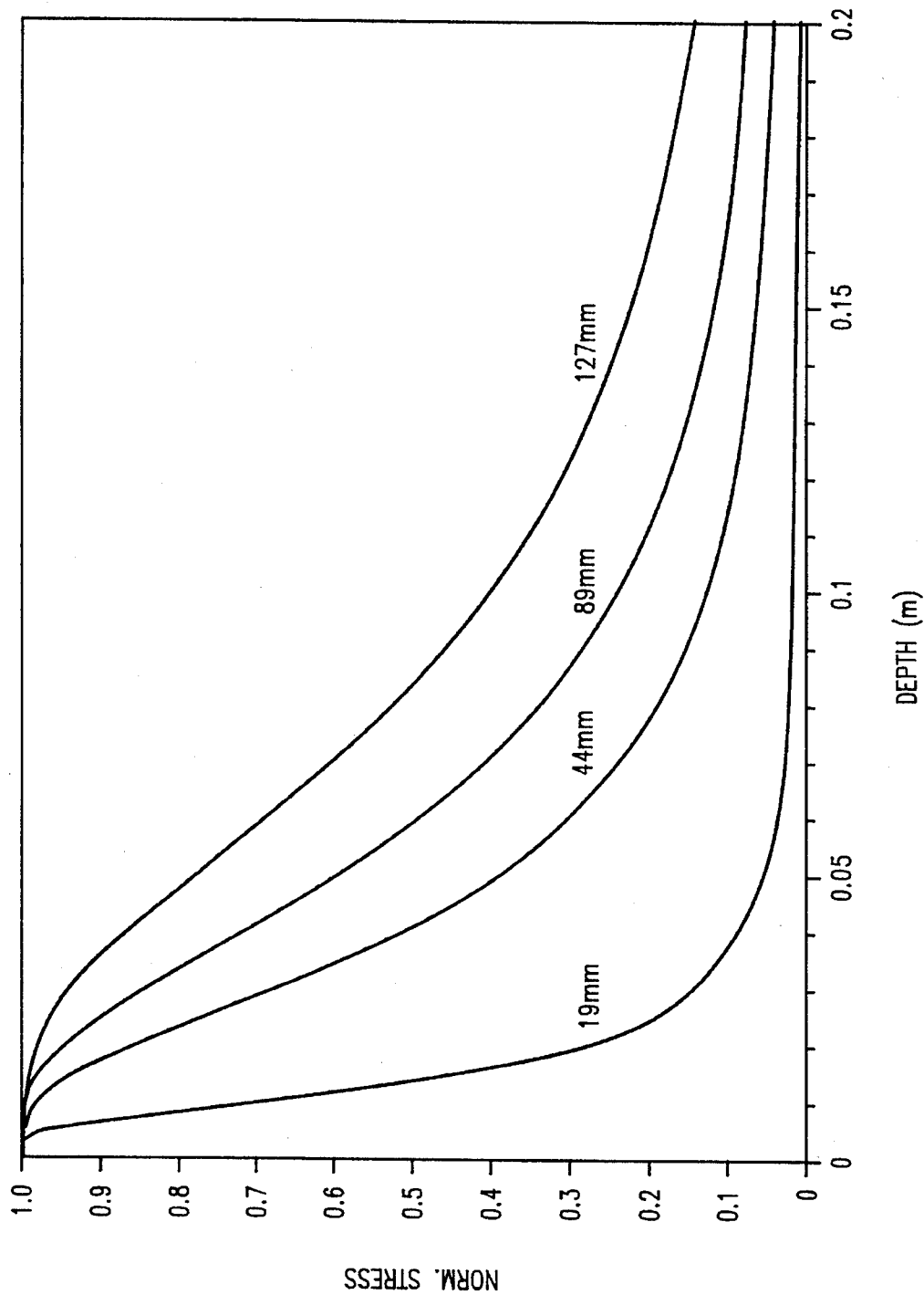
FIG. 3b shows the normalized stress in foam as a function of depth using various sizes of circular compressors.

Referring now to FIGS. 3a and 3b, another preferred embodiment of elastography can be illustrated. In this embodiment, the variation in stress based on depth is determined by application of an appropriate formula describing stress as a function of other known quantities, such as depth and the radius of the compressor.

It is known that the behavior of axial stress under some compressors may be analytically estimated. A solution for the axial stress under a circular compressor has been analytically derived, by extension of a solution to the Boussinesq problem, in Saada, Elasticity, Theory and Applications, Ch. 14 (Pergamon Press, N.Y. 1974), viz., $$\sigma(z) = \sigma(0)\left[\frac{z^3}{(a^2+z^2)^{3/2}} - 1\right], \quad \text{Equation 9}$$

where $\sigma(z)$ is the stress in the axial direction (where a negative value indicates an upward stress), $\sigma(0)$ is the uniformly distributed applied stress (where the total load is $\pi a^2 \sigma(0)$), a is the radius of the circular compressor, and z is the axial distance). Equation 9 may be rewritten as $$\sigma(z) = \sigma(0)\left[\frac{1}{\left[1+\left[\frac{a}{z}\right]^2\right]^{3/2}} - 1\right], \quad \text{Equation 10}$$

which emphasizes the fact that the stress profile is dependent only on the dimensionless ratio (z/a).

FIG. 3a illustrates a varying decrease in axial stress. The strain observed (line 1) in a foam phantom exhibits a varying decrease as a function of depth when a 127 mm circular compressor has been utilized. This observed strain corresponded well with the analytically estimated strain (line 2), derived by dividing the elastic modulus into the analytically determined variation in stress. Because the elastic modulus was approximately the same throughout the foam phantom, the values along lines 1 and 2 are in approximately direct proportion to the corresponding values for stress as a function of distance.

Figure 3C:
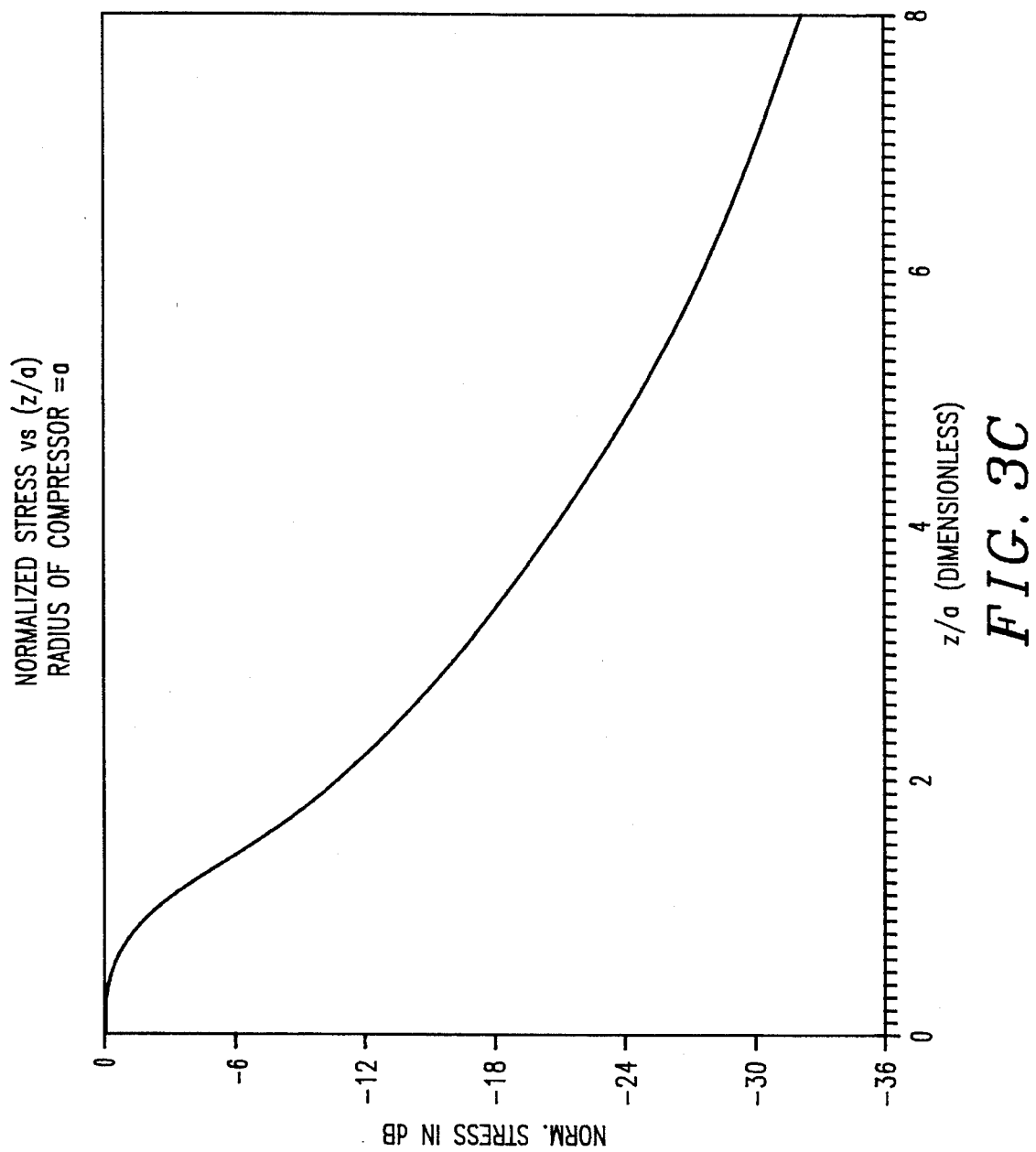
FIG. 3c shows the normalized stress in dB as a function of z/a, the depth divided by the area of a circular compressor.

FIG. 3b illustrates a plot of analytically derived stress profiles for circular compressors of varying size. The normalized stress ($|\sigma(z)/\sigma(0)|$) decreases rapidly for small compressors, attaining a relatively constant yet small value at a shallow depth. On the other hand, the stress profiles of larger compressors tend to drop progressively much more slowly. FIG. 3c further illustrates the normalized stress in dB as a function of the quantity (z/a), the ratio of the axial distance from the compressor and the radius of the circular compressor. It may be observed that only modest reductions in stress are encountered for values of (z/a) that are smaller than or equal to 1.

Figure 4A:
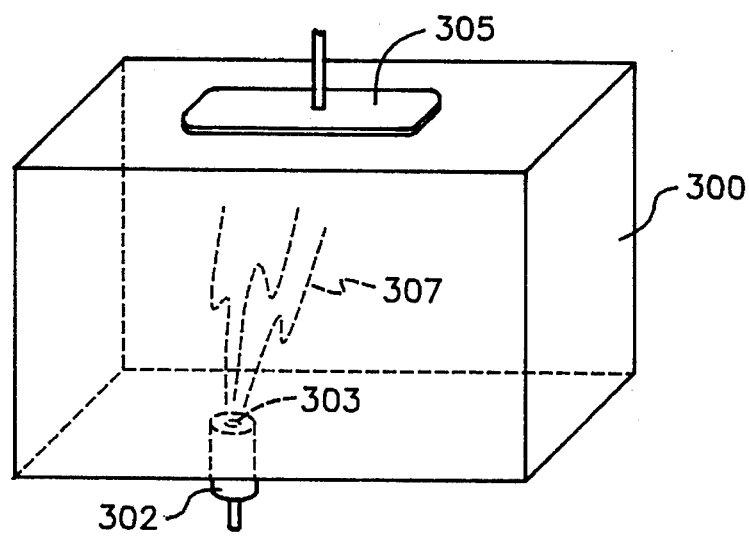
FIG. 4a shows a cross sectional view of an apparatus for determining stress distribution under a given compressor.
Figure 4B:
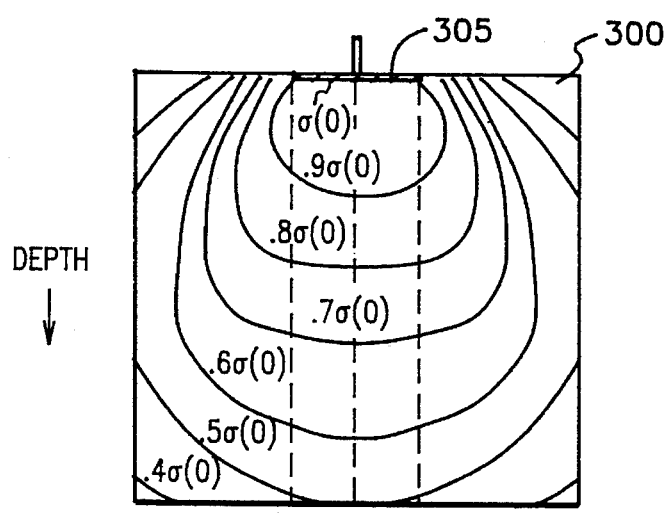
FIG. 4b shows a cross sectional view of a stress distribution under a compressor as a function of position relative to the compressor.

Formulas such as those derived by Saada for circular compressors may be derived for more complicated shapes (some of which have been derived in Saada, supra, Ch. 14). On and off axis, the stress distribution for a given compressor may also be experimentally derived. A preferred experimental method for deriving this stress distribution is illustrated in FIG. 4a. A transducer 301 with aperture 303 is sonically coupled to a target body 300 of known elasticity, preferably with an elasticity similar to that of the types of tissue that the compressor will be used with, opposite the compressor 305. An A-scan is then taken of the target body along sonic path 307. The compressor 305 is then compressed a known distance $\Delta y$, a second A-scan taken, and the stress profile determined from the elasticity and measured strain along the A-scan. After the stress distribution is determined along one A-scan, the compressor 305 is lifted from target body 300, moved laterally a known distance, and placed in contact with the target body 300 again. The stress distribution is then determined along the new (relative to the compressor) sonic path according to the same method as for the first sonic path. This process is repeated until a desired number of stress distributions have been obtained. Finally, a three-dimensional stress distribution for the compressor 305 is estimated based on the measured stress distributions. FIG. 4b illustrates what a cross-sectional plot of such an estimated stress distribution might look like in a target body.

The curves represent stress distribution isobars, with the value of the isobars being relative to the stress $\sigma(0)$ of the region in the target body immediately adjacent to the compressor 305.

In another embodiment, the target body 300 may also be moved, by known amounts, relative to transducer 301 and compressor 305. By moving the target body 300 certain distortions may be minimized, such as distortions that might result from repetitively measuring strain along a sonic path where fixed scatterers exist along that sonic path. In yet another embodiment, an array of transducers is used as both the compressor and transducer to interrogate itself, the array being fired both before and after compression, yielding measurements of the strain (and thus stress) distributions along the different sonic paths.

According to a presently preferred embodiment of elastography, after the stress distribution has been determined by one of the methods described above it is stored, such as by any conventional means like electronic or magnetic media or computer memory, for later recall. The stress distribution is subsequently recalled, following an elastographic measurement of a desired target body using the compressor 305. The appropriate amount of stress for each echo sequence segment of interest is then determined, by matching an echo sequence segment's known position relative to the compressor with the value for stress at the same relative position for the stress distribution. The compressibility of each segment may then be determined by applying the appropriate value of stress to the strain of the segment, where the strain may be determined from the measured time shifts in the echo sequences according to the elastographic method described above and the applied stress may be measured from a compliant layer in front of the transducer 301.

Figure 5A:
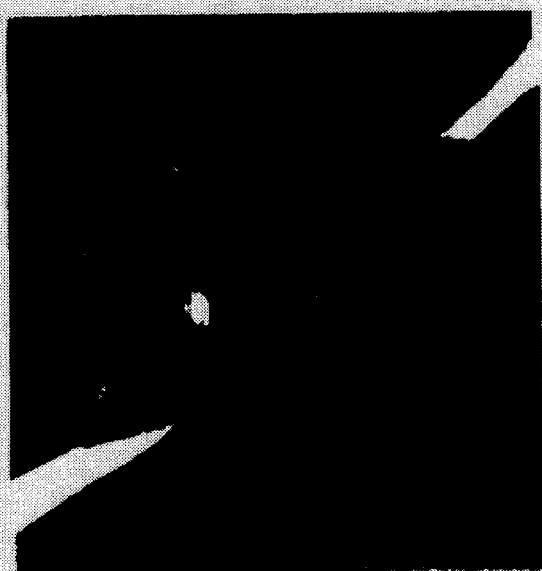
FIG. 5a shows a photograph of a phantom consisting of two triangular foam pieces joined along a diagonal seam.

To further explain this preferred embodiment, reference is made to FIG. 5a, showing a phantom consisting of two triangular foam pieces joined along a diagonal seam. This phantom was obtained by diagonally cutting a square foam block with a porosity of ~20 ppi, and then tightly joining the cut pieces. However, as seen in FIG. 5a, the diagonal seam is not visible when a B-scan was used (incidentally further showing the limitations of prior art B-scans as compared to elastograms).

Figure 5B:
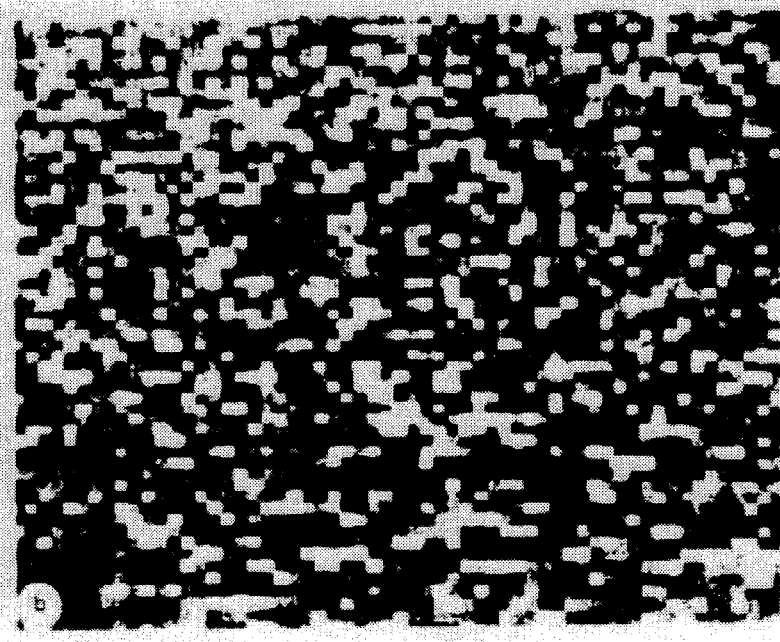
Figure 5E:
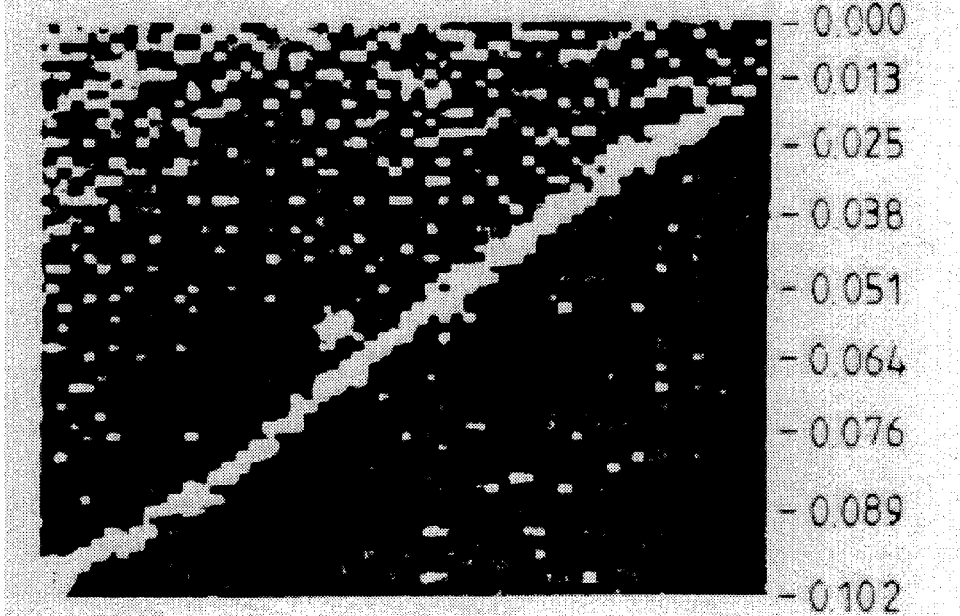
Figure 5F:
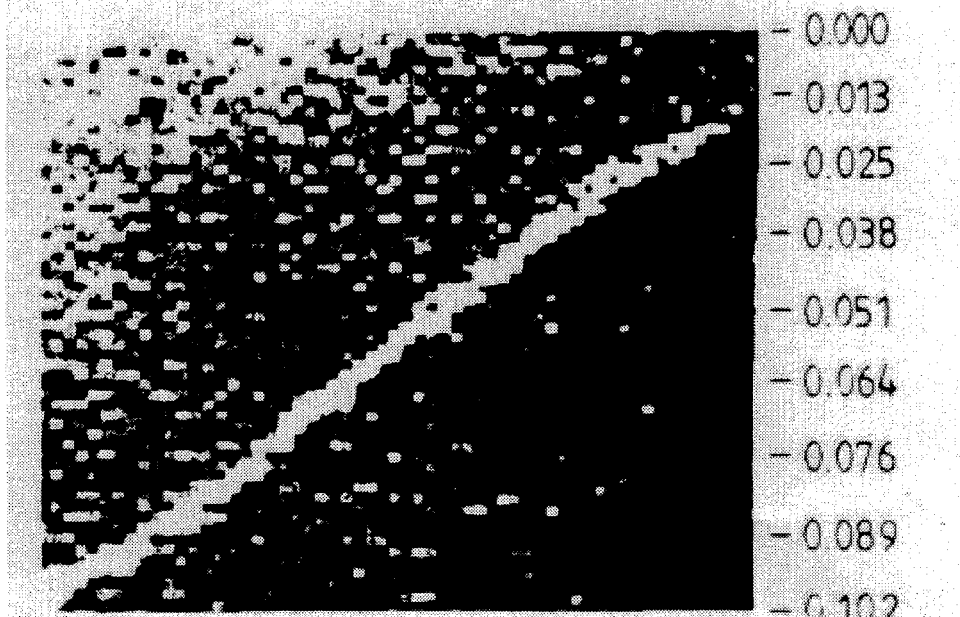

FIG. 5c shows an elastogram corresponding to the B-scan of FIG. 5b, but without any depth correction. Conventionally, the lighter shaded segments of the elastogram represent areas of higher compressibility, and the darker segments represent areas of lower compressibility. Clearly seen running diagonally through the elastogram is the diagonal seam. Further, this seam correctly shows up as a region of higher compressibility, because the surface along the seam contains a large number of open foam reticules which would be more compressible than the intact closed ones. While this elastogram shows surprising differentiation when compared with the B-scan of FIG. 5b, it is limited by the increasingly darker shading (representing decreasing compressibility) that occurs for segments more distant from the compressor and transducer. This effect arises, as previously noted, due to the assumption of uniform stress distribution made in earlier methods of elastography.

FIG. 5d shows an elastogram corresponding to FIGS. 5b and 5c using the depth-correction method described above. Because this method accounts for and factors the variations in stress as a function of depth with the measured strain, the decreasing compressibility seen in FIG. 5c no longer appears in FIG. 5d. Rather, the elastogram of FIG. 5d shows relatively uniform values for compressibility across all depths, as one would expect to find for a body composed of the same material.

A method is also provided, in a presently preferred embodiment of elastography, to correct for artifacts and image deterioration due to aberrations in the target body. Almost all ultrasonic imaging suffers from such artifacts and image deterioration, particularly from aberrations at the body wall. Interspersed layers of fat and muscle, having differing sonic velocities, may interfere with focusing and proper registration of ultrasonic beams.

A presently preferred method of correcting for any such distortions follows an initial determination, according to the elastographic methods already described, of the compressibility of each segment of interest in the target body. These compressibility profiles are then used to identify regions having differing sonic velocities. This identification is preferably computed from the compressibility profiles, but it may be done manually from an elastogram or, when identifying the boundaries of such regions, by a standard B-scan. For example, when dealing with a human body wall it is known that fat is much softer than muscle; this difference should show up clearly on compressibility profiles or elastograms, and either one may be used to identify the fatty versus muscle regions.

Once the regions are identified, a sound "speed map" of the regions of interest is calculated by ascribing the appropriate sonic velocities to the identified regions. For example, it is further known that one may generally ascribe a sonic velocity of about 1450 m/s to fatty regions and about 1580 m/s to muscle. Having identified which regions are fatty and which muscle, and the boundaries of these regions along each echo sequence of interest, a map of the varying sonic velocities along each sonic beam in an array of beams is made. Once the speed map is determined, the times required to traverse the segments along each sonic beam may be calculated and summed, yielding the time required for each echo sequence to traverse the body wall. The appropriate time delays, necessary to correct for variations in echo sequence travel time along different sonic beams through the same distance, are then determined. Finally, these delays are applied to correct each echo sequence and the derived compressibility profiles and elastograms of the target body.

While this method has particular application with respect to correcting distortion and shifts incurred by aberration at a body wall, it should be recognized that it may also be applied to other areas of target bodies, particularly where the varying regions of sonic velocity can be readily identified by initial compressibility profiles or elastograms. This method may be used to clarify both elastograms and sonograms.

In a preferred embodiment, the present invention also provides an elastography method for taking elastographic measurements in heterogeneous target bodies, such as a human breast, comprising multiple tissue regions having different ranges of elasticities.

Figure 9:
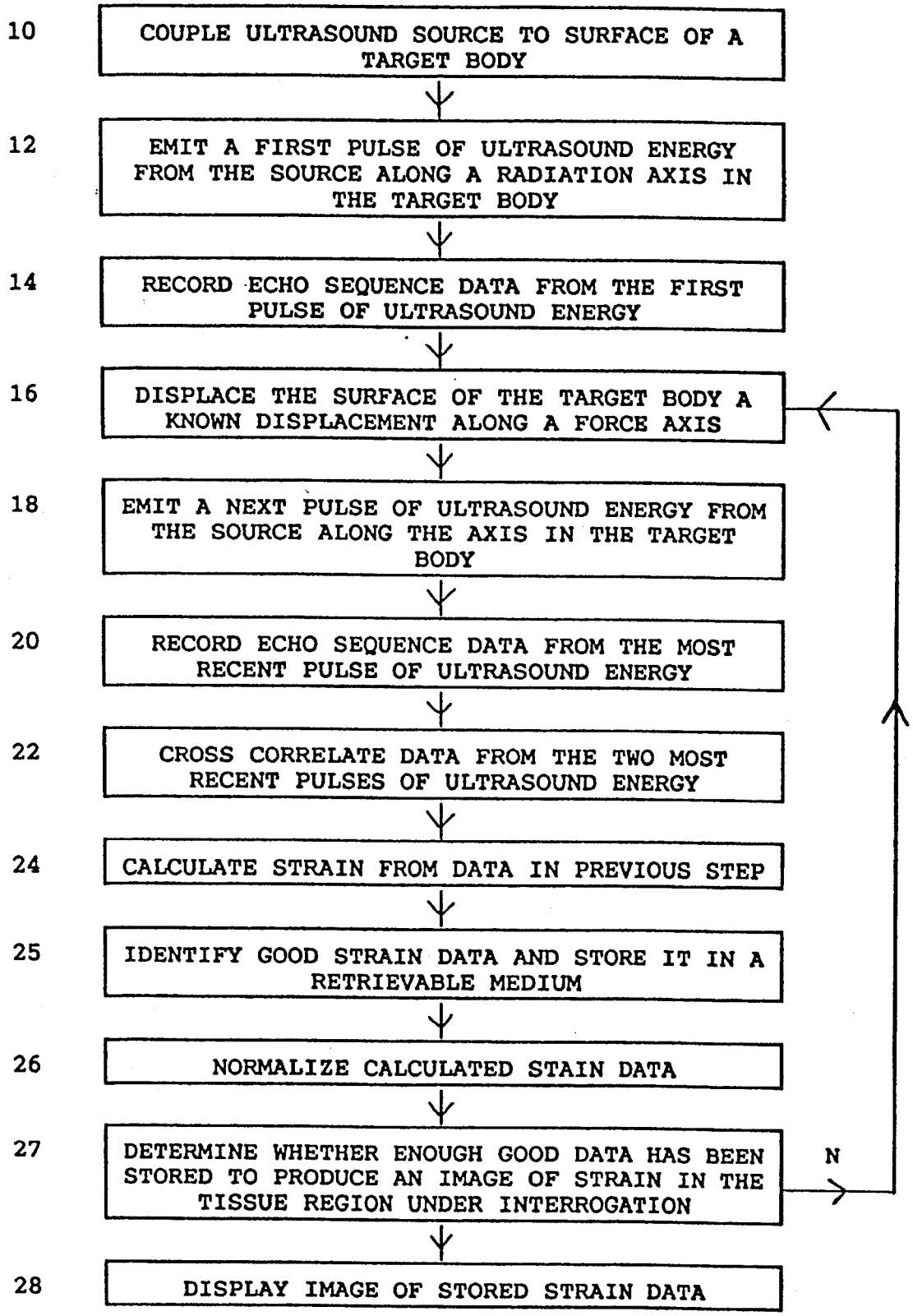
FIG. 9 is a block diagram of a method of practicing the present invention.

First, an ultrasonic source is sonically coupled to the surface of a target body, as shown in block 10 of FIG. 9. The source may be a single transducer or an array of transducers capable of emitting ultrasound energy in a preselected sequence at a preselected emission interval. A first pulse of ultrasonic energy is emitted from the source along a radiation axis in the target body, as shown in block 12 of FIG. 9. The arrival time of the echo sequence having at least one echo segment arriving in response to the first pulse of ultrasonic energy is recorded, as shown in block 14 of FIG. 9.

The surface of the target body is then displaced a known displacement, $\Delta X$, along a force axis so as to compress the target body, as shown in block 16 of FIG. 9. The surface of the target body may be displaced by (1) moving the ultrasonic transducer a known displacement, (2) moving another object that is also in contact with the surface of the target body a known displacement, (3) displacing a surface of the target body opposite from the surface where the transducer is coupled, or (4) projecting a sonic wave into the target body of sufficient intensity to result in a displacement of the surface of the target body. Another object capable of causing such displacement may be an inflatable coupling device that sonically couples the transducer to the surface of the target body. In such an instance, inflation or deflation of the coupling device resulting in a known displacement along the force axis will serve to displace the surface of the target body.

The displacement of the target body surface results in an elastic wave traveling through the target body surface along the force axis. The speed of the elastic wave is substantially less than the speed of the ultrasonic pulse in the target body. In a preferred method of practicing the present invention, the elapsed time between any two successive pulses of ultrasonic energy is large enough to allow the elastic wave to travel to the desired depth of interrogation within the target body.

A next pulse of ultrasonic energy is then emitted from the source along the axis in the target body, as shown in block 18 of FIG. 9. The arrival time of a next echo sequence arriving in response to the next pulse of ultrasonic energy and having at least one echo segment that is congruent with at least one echo segment that arrived in response to the first pulse is recorded, as shown in block 20 of FIG. 9. The differential displacement from at least one congruent echo segment from the two most recent pulses of ultrasonic energy is measured. In a preferred embodiment, the differential displacement is measured using a cross-correlation technique, as shown in block 22 of FIG. 9. Where the most recent pulse is pulse n, the differential displacement measurement is derived from pulses n-1 and n.

The present invention further involves calculating strain from the differential displacement data obtained in the prior step, as shown in block 24 of FIG. 9. This yields the calculated strain, CS. Good strain data that meets a predetermined quality standard is stored in a retrievable medium, as shown in block 25 of FIG. 9. The evaluation of strain data is a subjective evaluation for one of ordinary skill in the art, depending upon the particular circumstances of the target body under interrogation. This evaluation can be based upon the degree of overlap of the echo sequences that are evaluated using the cross-correlation technique.

The normalized strain, NS, is then calculated, as shown in block 26 of FIG. 9. Normalized strain data is data that is corrected or "normalized" to account for sensitivity limitations of the instrumentation used to measure differential displacement.

Due to the sensitivity limitations of this instrumentation, a certain amount of differential displacement may occur at each displacement interval, without being detected. It is not until the differential displacement for a series of displacement intervals exceeds the lower sensitivity threshold of the measuring instrumentation that a measurable differential displacement will be detected by the instrumentation.

Thus, the instrumentation readings and resulting strain calculations will tend to indicate a step increase in strain at the particular displacement interval at which the cumulative strain exceeded the sensitivity threshold of the instrumentation. This cumulative strain reading is normalized to spread it over the displacement intervals over which it has actually occurred.

At each displacement interval, n, the calculated strain, $CS_n$, is normalized by dividing that strain by the number of displacement intervals, n, that have occurred since the initiation of the most recent compression or decompression strokes. Thus, normalized strain is calculated by the following relationship:

$NS_n = CS_n/n$ where:

$NS_n$ = normalized strain at displacement interval n $CS_n$ = calculated strain at displacement interval n.

It is anticipated that in practicing this invention, good cross-correlation data will be found at different segments of the force axis for different degrees of compression. The steps depicted in blocks 16–27 of FIG. 9 are then repeated at least once. After each repetition, the operator determines whether enough good data has been stored to produce an image of the tissue region under interrogation, as shown in block 26 of FIG. 9.

One objective of the present invention is to obtain and display an image of the target body, as shown in block 28 of FIG. 9. This invention provides a means of obtaining such an image over a greatly enhanced dynamic range. At each given displacement interval, only a portion of the total dynamic range under investigation yields good strain data. This is why the subjective evaluation is made as to which cross-correlation data is stored in a retrievable medium.

In a preferred embodiment, an image of the stored strain data may be displayed using the Halo™ software package distributed by Media Cybernetics of Silver Springs, Md.

The total image may be thought of as comprising pieces, similar to a jigsaw puzzle. Each displacement may result in image portions being stored that relates to certain pieces of the jigsaw puzzle. One difficulty that arises in this method is that the position of the target body region under interrogation is shifted at each displacement. This shift is referred to as $\Delta TB_n$. Return-ing the jigsaw puzzle analogy, the image in the jigsaw puzzle is shifted at each displacement interval. Thus, the stored image data must be corrected in order to account for this displacement.

The strain at each displacement interval is equal to the shift of the interrogated target body region divided by the displacement of the surface of the target body along the force axis for that displacement interval. From this relationship, one of ordinary skill in the art can understand that the displacement of the interrogated target body region at each displacement interval can be calculated by the following relationship:

$$\Delta TB_n = \int_{X_o}^{X_n} NS_n \, dx$$

where:

$\Delta TB_n$ is the interrogated target body region displacement at displacement interval n;

$X_o$ is the initial displacement of the target body surface along the force axis;

$X_n$ is the displacement of the target body surface along the force axis at displacement interval n;

$NS_n$ is the normalized strain at displacement interval n; and dx is the differential displacement of the target body surface along the force axis.

Once $\Delta TB_n$ is ascertained at each displacement interval n, the stored strain data at each displacement interval n can be shifted by an amount equal to $\Delta TB_n$ in order to produce an image of the interrogated target body region.

Figure 7:
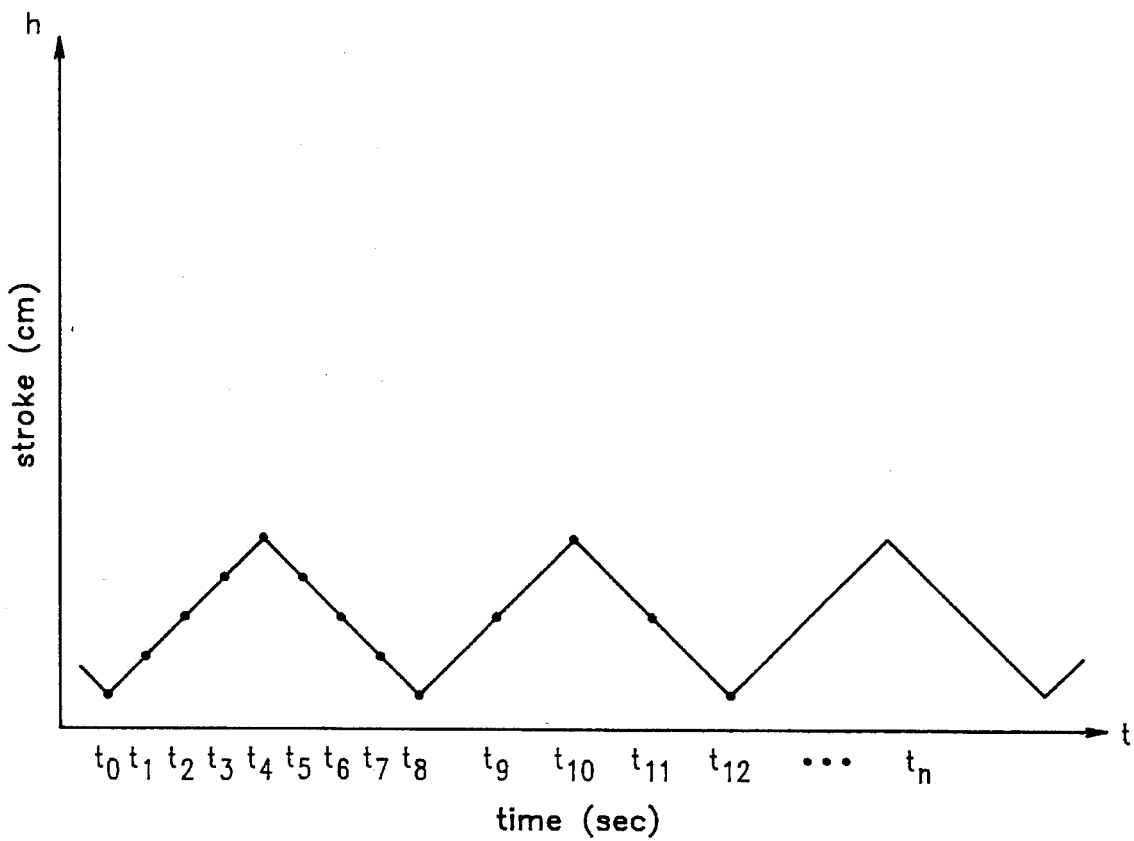
FIG. 7 shows a plot of echo sequence arrival times versus transducer displacement for the oscillatory method of measuring elastographic data of the present invention.

FIG. 7 depicts a graph showing arrival times for successive pulses as a function of ultrasonic source compression.

The total compression displacement or stroke is denoted by the symbol "h." The successive arrival times are denoted by the variables $t_0, t_1, t_3 \ldots t_8$.

In a further refinement of this embodiment of the invention, after the surface of the target body has been compressed by displacement h, it is then decompressed in known decompression increments of $\Delta X$ and the strain is calculated for successive arrival times, as it was calculated during the compression stroke. This compression and decompression sequence produces a periodic data plot such as a triangular data plot, as shown in FIG. 7.

During the compression stroke, the displacement intervals are counted from the initial displacement to the last compression displacement stroke, shown at $t_4$ in FIG. 7. Once the decompression stroke begins, the displacement interval counts, n, are started again and counted to the last decompression displacement stroke. Thus, for the data shown in FIG. 7, arrival times $t_1$–$t_4$ correspond to displacement intervals 1–4 while arrival times $t_5$–$t_8$ also correspond to displacement intervals 1–4.

The time period, T, shown in FIG. 7, is the period of the ultrasonic wave emitted from the transducer. The quantities h and t can be adjusted separately. The time increments $t_0, t_1 \ldots t_n$ are of a sufficient duration to allow a full frame of RF data to be acquired.

Figure 6:
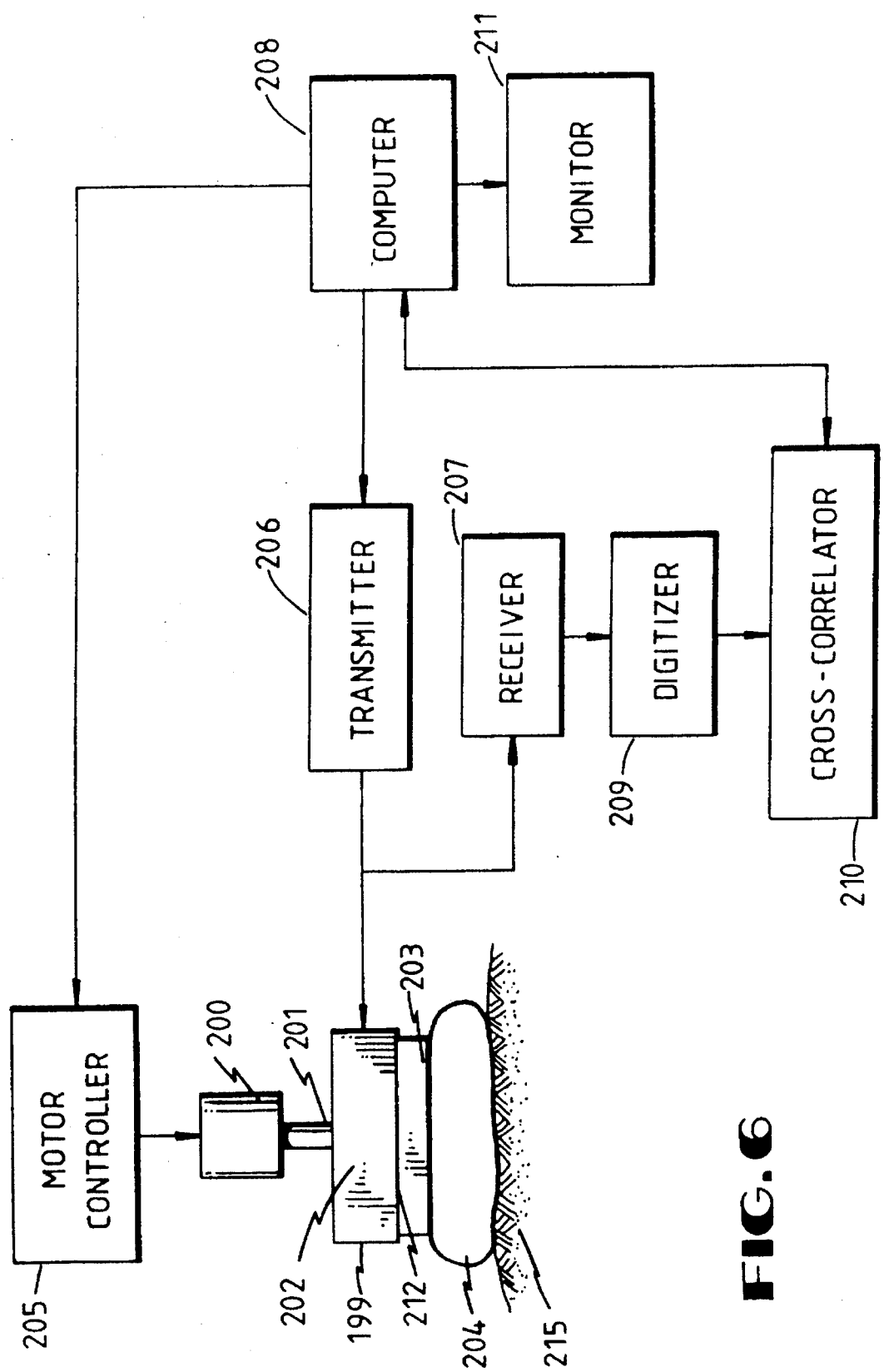
FIG. 6 shows an embodiment of an apparatus in which a compressor is coupled to a target body for purposes of experimentally determining the variations of stress with depth in the target body.

Referring now to FIG. 6, an apparatus is shown schematically for determining compressibility of a target body 204 comprising a rigid frame 199; a motor 200 attached to the frame 199; an axial member 201 having a first and second end, the first end being coupled to the rigid frame 199, and the second end being coupled to the motor 200 such that the axial position of the axial member 201 and rigid frame 199 may be varied by operating the motor 200; and an ultrasonic source 202 mounted on the rigid frame 199. The ultrasonic source 202 has a surface 212 capable of being sonically coupled to the target body 204. The target body 204 rests on a support 215.

The ultrasonic source 202 may be a single transducer or a transducer array. The axial member 201 may be a worm gear.

The top surface of a layer 203 with a known elastic modulus and speed of sound may be coupled to the ultrasonic source's 202 lower surface 212. The bottom surface of the layer 203 is coupled to the target body 204.

The apparatus may also contain a data storage medium connected to the transducer for storing signals from the transducer. The movement of the axial member 201 may be controlled in precise amounts by using a motor controller 205 connected to the motor 200, such that operation of the motor 200 moves the axial member 201 in precise amounts.

A transmitter 206 may be connected to the ultrasonic source 202 to energize the ultrasonic source 202. A receiver 207 may also be connected to the ultrasonic source 202 such that signals generated by the ultrasonic source 202 in response to echo sequences are transmitted to the receiver 207. A digitizer 209 may be connected to the receiver 207 to convert analog signals into numerical data. Furthermore, a cross-correlator 210 may be connected to the digitizer 209. A computer 208 may be connected to the transmitter 206 such that the computer 208 is capable of triggering the transmitter 206. Also, the cross-correlator 210 may be connected to the computer 208 such that data may be received by the computer 208. In a preferred embodiment, the cross-correlation may be accomplished by using a software program instead of a hardware cross-correlator 210, such that the cross-correlation algorithms discussed above may be implemented, by any well-known programming technique. The computer 208 may be programmed to convert the numeric data, representing echo sequences, into strain or compressibility data or into a strain or compressibility profile. Images of the strain profile and the compressibility profile may be displayed on a monitor 211 connected to the computer 208.

It will be noted that the motor controller 205 and motor 200 may be rigidly connected to additional structure, such that ultrasonic source 202 may only be moved as the axial number 201 or additional structure is moved. It will also be noted that the portion of the apparatus including the motor controller 205, motor 200, axial number 201, rigid frame 199 and ultrasonic source 202 may be hand held, where the motor 200 may still axially move the axial member 201 and ultrasonic source 202 while said portion of the apparatus is being held in a hand against the target body 204.

Further, instead of being in a handheld device, the ultrasonic source 202 may be enclosed in any convenient means, such as a balloon, for insertion inside target bodies. This latter apparatus would have particular application in examinations for diseases such as prostate cancer, which may not appear clearly on normal sonograms. In such an application, the ultrasonic source 202 may be attached to a flexible control cable and surrounded by a balloon. The balloon and ultrasonic source 202 may then be inserted into the rectum, with the flexible control cable connecting the ultrasonic source to the portion of the apparatus remaining outside of the body. A fluid may then be used to inflate the balloon inside the rectum, and to further inflate the balloon to compress against the walls of the intestinal tract. A means for rotating the ultrasonic source 202 inside the balloon may also be used for positioning the ultrasonic source to insonify particular tissues of interest, such as the prostate, within the body. Pre- and post-compression echo sequences may then be made and analyzed by the computer to determine the strain profile for the tissue of interest. Further, a compliant body of known elasticity may be disposed such that it is compressed between the balloon and the intestinal wall, allowing the stress from the compression to be estimated and a compressibility profile to be determined.

Figure 8:
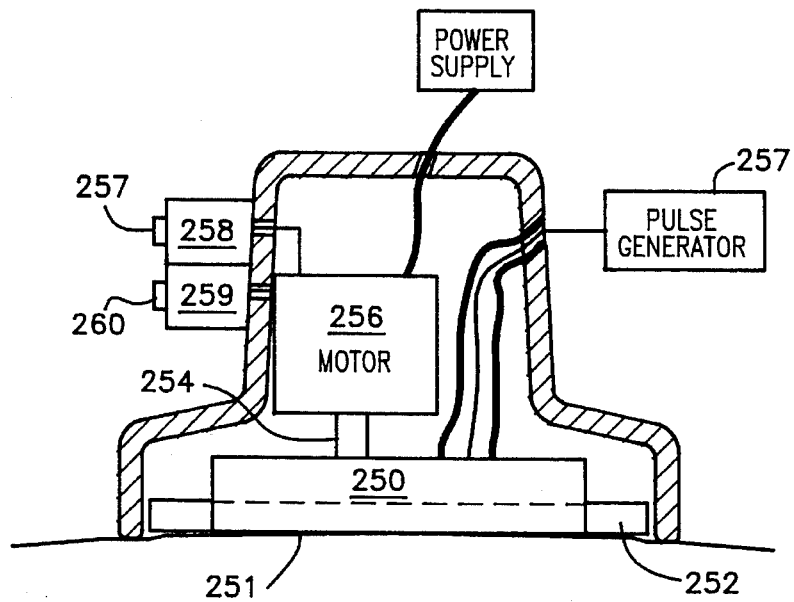
FIG. 8 shows an apparatus embodiment for practicing the oscillatory method of the present invention.

Another apparatus embodiment of the present invention is particularly suited for use in taking elastographic measurements of a heterogeneous target body is shown in FIG. 8. This apparatus embodiment comprises an ultrasonic transducer 250 capable of emitting and receiving pulses of ultrasonic energy. The portion of the transducer intended for coming into contact with the target body is the base of the transducer 251. A pulse generator 257 is electrically connected to the ultrasonic transducer. The pulse generator is capable of generating pulses of ultrasonic energy to be emitted by the ultrasonic transducer. A shaft or axial member 254 having a first and second end is mechanically coupled at its first end to the transducer. A shaft driver device 256 is mechanically coupled to the second end of the shaft. The shaft driver device is capable of extending and/or retracting the shaft and transducer in preselected displacement increments at preselected speeds. A shaft displacement controller 259 is coupled to the shaft driver device. The shaft displacement controller 258 is capable of adjusting the magnitude of the displacement increment that the shaft driver device extends or retracts said shaft and said transducer in response to an input selection. A shaft speed controller 258 is coupled to the shaft driver device. The shaft speed controller is capable of adjusting the speed at which the shaft and transducer are moved by the shaft driver device in response to an input selection.

As shown in FIG. 8, in a preferred embodiment: (1) the shaft driver device is a stepper motor; (2) the shaft displacement controller is a motor controller comprising an externally mounted displacement selector 260 capable of receiving an input selection; and (3) the shaft speed controller is a motor controller comprising an externally mounted speed selector 257 capable of receiving an input selection. In this preferred embodiment, the externally mounted displacement selector and the externally mounted speed selector can be control knobs as shown in FIG. 8, or adjustable digital displays, or control levers.

In a preferred embodiment, the shaft displacement controller, shaft speed controller, and the stepper motor are housed together in a housing. In this preferred embodiment, a displacement selector and a speed selector are externally mounted on the outside of the housing comprising the shaft speed controller and shaft displacement controller.

The shaft displacement controller and shaft speed controller may also be programmable. They may be independently programmed or programmed such that one variable, such as shaft speed, changes as a function of another variable, such as shaft displacement.

In another preferred embodiment of the present invention, a plate or shoe 252 having an outer perimeter greater than the outer perimeter of the base of the transducer is attached to the base of the transducer. The plate enlarges the surface area of compression/decompression thereby providing more uniform stress in the target body or tissue region under elastographic interrogation. In a preferred embodiment, the plate has a rigid central region.

The transducer, shaft, and shaft driver device may all be housed within an outer housing such that the shaft driver device is mounted in a fixed position within the housing. This housing will allow for hand-held operation of this apparatus embodiment. It is also understood, that a transducer array may be used in the place of a single transducer in practicing this apparatus embodiment of the present invention. In the transducer array embodiment, a multiplicity of transducers may be energized or fired to emit ultrasound pulses at each displacement interval. These multiple firings may be simultaneous or sequential.

Although elastography has been described in relation to clinical diagnosis above, this should be understood not to be a limiting factor on the utility of elastography. For example, elastography may be used in forensics, tissue characterization studies, veterinary medicine, laboratory experiments, and industrial applications. Also, the present techniques may be employed to any materials that are capable of being physically compressed or displaced; that is, a material which is internally displaceable in response to pressure applied to the material.

The various aspects of elastography will appear more specifically in the following examples that are purely illustrative and should not be construed to limit the scope of the invention. These examples are based on experiments performed to corroborate the basic elastographic method. All experiments were performed in a 120 gallon water tank on synthetic foam blocks and tissues in vitro. The experimental setup included a system controlled by a Compaq 386 computer via an IEEE 488 bus. A stepper motor controller (made by Superior Electric Co.) enabled transducer movements in steps of 2.5 microns. A transmitter (made by Metrotek Corp.) was used to shock excite the transducer. The received signal was amplified by an input protected, TGC controllable amplifier, and fed into an 8 bit digitizer operating at 50 MHz (made by LeCroy Corp.). The Compaq computer was used to compute the digitized data, using a program, written using ordinary program techniques, which included routines which substantially implemented the cross-correlation algorithm disclosed in Boucher et al., supra. A NEC monitor with a 256 gray shade scale display was used to display the A-lines, B-lines and elastograms. All experiments were performed using a 2.25 Mhz, 19 mm diameter transducer focused from 7–19 cm.

EXAMPLE 1

Measurement of elastic modulus of foam blocks

Three types of reticulated open cell polyester foam samples were cut into 14×14×5 cm blocks. Type I was a black foam with a porosity of ~80 ppi (pores per inch). Type II was a fellow foam with a porosity of ~30 ppi. Type III was a coarse black foam with a porosity of ~20 ppi. The foam blocks were immersed in a beaker containing distilled water and a small amount of a surfactant Coy Bath-kleer, Instrumentation Laboratories, Lexington, Mass.). The foam blocks were then degassed under laboratory vacuum (~0.5 bar) for approximately 30 minutes, and then transferred to a large water tank maintained at 21°±1° C. The elastic modulus of each foam block was determined by uniformly loading the top of the foam with 6 premeasured lead weights with masses of 50, 100, 150, 200 250, and 300 grams. The resultant compression of the foam was measured from the difference between the times of flight of an ultrasonic pulse to and from a reference plane before and after loading. The elastic modulus of each foam block was calculated from the mean of their respective stress/strain data obtained for the above mentioned loads.

The elastic moduli values were calculated for compression only and not for expansion. The resulting mean values of the elastic moduli for foam Type I was ~23 kPa; for foam Type II it was ~38 Kpa; and for foam Type II it was ~21 kPa. The standard deviation in these measurements was on the order of ±20%. The inverse elastic moduli values in the three foam blocks were 0.043, 0.026, and 0.048 $kPa^{-1}$, respectively.

EXAMPLE 2

Measurement of axial stress uniformity

A block of Type III foam was degassed and immersed in the water tank at room temperature. An annular plexiglas plate was attached to the transducer. The flat surface of the transducer aperture formed a part of the compressor, whose size could be changed by using a different size annulus. Annuli were made with outer diameters (o.d.) of 44, 89 and 127 mm. For each annulus, the strain profile in the foam in response to a 1 mm compression was measured.

As mentioned earlier, the extension of the 1-dimensional model to the 3-dimensional case involves assumption of uniform axial stress field. However, this assumption is strictly valid only for infinitely large compressors. The theoretical behavior of the axial stress as a function of the quantity (z/a), the ratio between the axial distance from the compressor aperture and the radius of the circular compressor, has been discussed above. This behavior is likely to become important for large values of (z/a). But, for ratios of $z/a \leq 1$, a relatively modest and gradual decline in the axial stress occurs, which could be either ignored or corrected for, as needed.

Since it was not feasible to make direct localized stress measurements, the axial distribution of strain was measured instead and assumed to be proportional to stress. The results of the axial strain in foam Type III is shown in FIG. 3a for a 127 mm compressor. Similar axial strains were taken for 44 and 89 mm compressors. From these experiments it became clear that the general behavior of the strain follows the theoretical predictions reasonably well.

EXAMPLE 3

Elastography in phantoms

Three foam phantoms were used to demonstrate the capabilities of elastography. The first phantom consisted of an 11 degree, 140 mm long wedge of foam Type I surrounded by blocks of foam Type II. The bottom part of the phantom was made of foam Type I. The second phantom consisted of two nearly identical triangular foam pieces obtained by diagonally cutting a square foam block of Type III and then tightly rejoining the cut pieces. The third phantom consisted of a 38 mm thick horizontal layer of foam Type I embedded between two foam blocks of Type II.

The elastography experiments were conducted by using the 127 mm o.d. annulus. The compressor was put in contact with the phantom and one A-line was taken. The compressor was then moved axially downward by 1.00 mm, and a second A-line was taken. The compressor was then lifted by several millimeters to clear the phantom, and moved laterally by 1 or 2 mm. The process was then repeated, until 40–60 A-line pairs were collected from a 40–120 mm wide region.

The A-line pairs were then cross-correlated and a strain image of the wedge phantom made, in which the wedge was clearly visualized. A "B-scan" was also constructed from the same raw data, but this B-scan yielded speckle and poor visibility of the wedge. Next, an elastogram of the wedge was derived from the strain image. The gray levels in the elastogram were calibrated in $kPa^{-1}$ units, and were derived from the strain image by estimating the average strain in the first 5 mm of the known anterior foam material. This strain was multiplied by the known elastic modulus of the first layer, and the resulting stress was assumed to be the stress applied to the system.

Similarly, a strain image of the second phantom, consisting of two triangular foam pieces and shown in FIG. 5a, was made. The seam between the foam pieces was clearly visible. The "B-scan" derived from the same data, shown in FIG. 5b, produced an image where the seam in the foam was completely invisible. FIG. 5c shows the corresponding elastogram, and FIG. 5d shows the elastogram after the application of correction for depth dependent stress.

The phantom images reveal several interesting and potentially useful characteristics of elastography. The strain image of the second phantom demonstrated that the background texture of the image tends to be much more uniform than a "B-scan" due to the apparent lack or diminution of speckle. Speckle is a known artifact which is present in all ultrasound B-scans, and which limits the attainable image quality. This strain image also demonstrated the sensitivity of elastography, where the thin region along the cut surfaces of the two foam blocks shows up clearly against the background. Evidently, cutting the foam results in severed and disrupted foam reticules. As a result, the region near the cut surface would be expected to contain a large percentage of open reticules which would be more compressible than the intact closed ones. By comparison, the "B-scan" image of the same structure shown in FIG. 5b is dominated by speckle and does not show the seam in the foam block, since the backscatter characteristics of the seam remain unchanged. Another result is the apparent good lateral resolution along the whole range from the face of the transducer, as demonstrated by the relatively uniform thin line representing the image of the seam. Since the transducer focal region extended from 7 to 19 cm, part of the phantom was in the near zone of the transducer and thus a significant broadening of the seam image would have been expected at close ranges. FIG. 5c shows a quantitative elastogram, where the slight vertical streaks are artifacts due to uncertainty in the estimation of the strain in the proximal 5 mm foam layer. FIG. 5d shows the effect of the theoretical correction for circular compressors, based on Saada's derivation, discussed above.

The strain image of the wedge phantom showed that the compressibility in the wedge was higher than that in the surrounding material. The increased compressibility along the cut wedges of the foam pieces was also demonstrated as an enhanced outline of the wedge. The corresponding "B-scan" showed a mottled appearance of the wedge, which was again dominated by speckle. It is worth noting that, in general, the wedge need not be visible on the "B-scan" in order to give a good elastogram (as was seen by the case of the diagonal seam in the second phantom). The fact that the backscatter from the wedge material is higher than that of the surround was fortuitous. The corresponding elastogram of the wedge demonstrated the ability of the technique to generate quantitative images of the elastic modulus distribution in the target. Similar images may be especially useful for diffuse disease in humans, where hardening or softening of whole organs would result in overall quantitative brightness changes in the image. The strain image of the third phantom showed a clear delineation and an excellent ability to visualize a 6 dB change in the elastic modulus of the soft middle layer, reduction of speckle, and the cut edge softening effect. The corresponding "B-scan" showed speckle and poor visibility of the layer.

EXAMPLE 4

Elastography in a bacon slab

A commercial vacuum-packed slab of bacon was tested in the water tank at 30°±0.5° C. The transducer was used along with an 89 mm annulus. Slight precompression was used in order to ensure tight contact between the compressor and the top surface of the slab. This was followed by a 0.5 mm compression along 40 parallel axial directions laterally separated by 1 mm. The resulting echo sequences were converted into digital data, processed by the computer, and displayed on the NEC monitor both as a standard B-mode image and as a strain image. Because of the relatively small z/a ratio ($\leq 1$), no correction for depth dependent stress distribution was applied.

The images of the bacon slab demonstrated that the principles of elastography can be practiced on biological tissues as well. Bacon is a good example, since fat is known to be generally softer than muscle. The strain image showed at least two dark (hard) layers in the proximal half of the image which probably correspond to the muscle layers in the specimen. The distal half of the image tends to indicate softer fatty structures. It was noted, however, that different fat layers in the slab appeared to possess varying degrees of compliance. The corresponding B-mode image was quite difficult to interpret.

These experiments are illustrative of, and should not be taken as limitations on, an apparatus and method of elastography. Thus, for example, it is noted that 8-bit digitizers are not required in elastography, as signals with more or less than 8 bits may be used. Similarly, digitizers may operate at frequencies other than 50 MHz, and have been operated as high as 200 MHz with elastography, with the well-known trade-off of more precision in the data versus larger sample data sizes as the frequency increases. Further, transducers other than 2.25 MHz transducers have been utilized, and in particular, 3.5 MHz and 5 Mhz transducers have been utilized and observed to yield more precise data than the 2.25 MHz transducer used in the above experiments.

It will be recognized that elastography may be practiced and modified in many ways. For example, it is well known that ultrasonic transducers are available in matched sets wherein a plurality of matched transducers are assembled side-by-side in a single head. It is contemplated that such multi-channel arrays may be coupled to an animal tissue or other compressible solid material, and that multiple ultrasonic signals may thereby be transmitted into the material simultaneously along an array of radiation axes. Thus, an entire section of the material may be examined by using such an array. Images of strain and/or elastic modulus may be made.

It will also be recognized that one transducer may be used as a transmitter and that one or more transducers may be offset from the transmitter and used as receivers.

While elastography has been shown in connection with certain presently preferred embodiments thereof, those skilled in the art will recognize that many modifications may be made therein without departing from the true spirit and scope of the invention. Accordingly, it is intended that the following claims cover all equivalent modifications and variations as fall within the spirit and scope of the invention.

We claim:

1. A method for taking elastographic measurements of a heterogeneous target body comprising the steps of:
   (a) sonically coupling an ultrasonic source to the surface of a target body;
   (b) emitting a first pulse of ultrasonic energy from the source along a radiation axis in the target body;
   (c) recording the arrival time of the first echo sequence having at least one echo segment arriving in response to said first pulse of ultrasonic energy;
   (d) displacing the surface of the target body a known displacement, $\Delta X$, along a force axis so as to compress the target body;
   (e) emitting a next pulse of ultrasonic energy from the source along said radiation axis in the target body following said movement;
   (f) recording the arrival time of a next echo sequence arriving in response to said next pulse of ultrasonic energy, said echo sequence having at least one echo segment that is congruent with at least one said echo segment that arrived in response to the preceding pulse;
   (g) measuring the differential displacement from at least one congruent echo segment of the two most recent pulses of ultrasonic energy;
   (h) calculating the strain from the differential displacement data obtained in step (g);
   (i) storing strain data that meets a predetermined quality standard in a retrievable medium;
   (j) normalizing the calculated strain data stored in step (i) using the formula:
   $NS_n = CS_n/n$ where:
   $NS_n$ = normalized strain at displacement interval n
   $CS_n$ = calculated strain at displacement interval n; and
   (k) repeating steps (d)–(j) until enough strain data has been stored to produce an image of the tissue body region under interrogation.

2. The method of claim 1, wherein said target body is a tissue body.

3. The method of claim 1, wherein the differential displacement is measured by a cross-correlation technique.

4. The method of claim 1, wherein the differential displacement is measured by a phase of the analytic signal.

5. The method of claim 1, wherein the differential displacement is measured by a phase of the cross-spectrum.

6. The method of claim 1, wherein said sonic coupling is achieved by placing an adjustable volume coupling device between the transducer and the surface of the target body.

7. The method of claim 6, wherein said coupling device is volume adjustable by inflation and deflation.

8. The method of claim 6, wherein the surface of the target body is displaced by changing the volume of the coupling device.

9. The method of claim 1, further comprising the steps of:
   (a) displacing the surface of the target body a known displacement, $\Delta X$, along the force axis so as to decompress the target body;
   (b) emitting a next pulse of ultrasonic energy from the source along the radiation axis in the target body following said movement;
   (c) recording the arrival time of a next echo sequence arriving in response to said next pulse of ultrasonic energy, said echo sequence having at least one echo segment that is congruent with at least one said echo segment that arrived in response to the preceding pulse;
   (d) measuring the differential displacement from at least one congruent echo segment of the two most recent pulses of ultrasonic energy;
   (e) calculating the strain from the differential displacement data obtained in step (d);
   (f) storing strain data that meets a predetermined quality standard in a retrievable medium;
   (g) normalizing the calculated strain data stored in step (f) using the formula:
   $NS_n = CS_n/n$ where:
   $NS_n$ = normalized strain at displacement interval n
   $CS_n$ = calculated strain at displacement interval n; and
   (h) repeating steps (a)–(g) until the number of decompression intervals equal the number of compression intervals.

10. The method of claim 9, wherein each displacement of the surface of the target body results in an elastic wave traveling within the target body.

11. The method of claim 10, wherein the elapsed time between the emission of the first and last pulse of ultrasonic energy from the source is large enough to allow the elastic wave to travel to the desired depth of interrogation within the target body.

12. The method of claim 1 further comprising the step of calculating the displacement shift of the interrogated target body region from its initial position at each displacement interval, $\Delta TB_n$, using the following formula:

$$\Delta TB_n = \int_{X_o}^{X_n} NS_n \, dx$$

where:
$\Delta TB_n$ is the interrogated target body region displacement at displacement interval n;

$X_o$ is the initial displacement of the target body surface along the force axis;

$X_n$ is the displacement of the target body surface along the force axis at displacement interval n;

$NS_n$ is the normalized strain at displacement interval n; and dx is the differential displacement of the target body surface along the force axis.

13. The method of claim 12, wherein the equation for calculating the displacement shift of the interrogated target body region is solved numerically.

14. The method of claim 1, wherein said ultrasound source comprises an array of transducers capable of emitting ultrasound energy in a preselected sequence at a preselected emission interval.

15. A method for taking elastographic measurements of a heterogeneous target body comprising the steps of:

(a) sonically coupling an ultrasonic source to a target body;

(b) emitting a first pulse of ultrasonic energy from the source along a radiation axis in the target body;

(c) recording the arrival time of the first echo sequence having at least one echo segment arriving in response to said first pulse of ultrasonic energy;

(d) moving the ultrasonic source a known displacement, $\Delta X$, along a force axis so as to compress the target body;

(e) emitting a next pulse of ultrasonic energy from the source along the radiation axis in the target body following said movement;

(f) recording the arrival time of a next echo sequence arriving in response to said next pulse of ultrasonic energy, said echo sequence having at least one echo segment that is congruent with at least one said echo segment that arrived in response to the preceding pulse;

(g) measuring the differential displacement from at least one congruent echo segment of the first pulse and most recent pulse of ultrasonic energy;

(h) calculating the strain from the differential displacement data obtained in step (g);

(i) storing strain data that meets a predetermined quality standard in a retrievable medium;

(j) normalizing the calculated strain data stored in step (i) using the formula:

$NS_n = CS_n/n$ where:

$NS_n$ = normalized strain at displacement interval n $CS_n$ = calculated strain at displacement interval n; and (k) repeating steps (d)–(j) until the ultrasonic source has traveled a desired compression distance;

(l) moving the ultrasonic source a known displacement, $\Delta X$, along the force axis so as to decompress the target body;

(m) emitting a next pulse of ultrasonic energy from the source along the radiation axis in the target body following said movement;

(n) recording the arrival time of a next echo sequence arriving in response to said next pulse of ultrasonic energy, said echo sequence having at least one echo segment that is congruent with at least one said echo segment that arrived in response to the preceding pulse;

(o) measuring the strain from at least one congruent echo segment of the first pulse and most recent pulse of ultrasonic energy;

(p) calculating the strain from the differential displacement data obtained in step (o);

(q) storing strain data that meets a predetermined quality standard in a retrievable medium;

(r) normalizing the calculated strain data stored in step (q) using the formula:

$NS_n = CS_n/n$ where:

$NS_n$ = normalized strain at displacement interval n $CS_n$ = calculated strain at displacement interval n; and (s) repeating steps (l)–(r) until the ultrasonic source has traveled a desired decompression distance.

16. The method of claim 15, wherein the displacement is measured by a cross-correlation technique.

17. The method of claim 15, wherein the strain is measured by a phase of the analytic signal.

18. The method of claim 15, wherein the strain is measured by a phase of the cross-spectrum.

19. The method of claim 15, further comprising the step of displaying an image of the stored strain data.

20. The method of claim 15, wherein the compression distance that the ultrasonic source is moved is equal to the decompression distance that the ultrasonic source was moved.

* * * * *

UNITED STATES PATENT AND TRADEMARK OFFICE
CERTIFICATE OF CORRECTION

PATENT NO. : 5,474,070
DATED : December 12, 1995
INVENTOR(S) : Jonathan Ophir et al.

It is certified that error appears in the above-indentified patent and that said Letters Patent is hereby corrected as shown below:

Title page, item [56] under "OTHER PUBLICATIONS" delete "Threep" and substitute --Three--.

At column 1, line 5, please delete "pan" and substitute --part--.

At column 1, line 7, please delete "pan" and substitute --part--.

At column 3, line 26, please delete "relates" and substitute --related--.

At column 3, line 54, after "thorax" please insert a comma.

At column 9, line 47, please delete "area" and substitute --radius--.

At column 13, line 16, please delete "fourier" and substitute --Fourier--.

At column 18, bridging lines 11-16, Equation 10 should read $$\sigma(z) = \sigma(0) \left[ \frac{1}{\left[1 + \left[\frac{a}{z}\right]^2\right]^{3/2}} - 1 \right]$$

UNITED STATES PATENT AND TRADEMARK OFFICE
CERTIFICATE OF CORRECTION

PATENT NO. : 5,474,070
DATED : December 12, 1995
INVENTOR(S) : Jonathan Ophir et al.

It is certified that error appears in the above-indentified patent and that said Letters Patent is hereby corrected as shown below:

At column 22, line 32, please delete "Return-ing" and substitute --Returning--.

At column 29, line 7, please delete "Mhz" and substitute --MHz--.

Signed and Sealed this

Twenty-third Day of April, 1996

Attest:

BRUCE LEHMAN

Attesting Officer

Commissioner of Patents and Trademarks